United States Patent
Kaplan et al.

(10) Patent No.: US 10,668,104 B2
(45) Date of Patent: Jun. 2, 2020

(54) BROWN ADIPOCYTE MODIFICATION

(71) Applicants: Ethicon Endo-Surgery, Inc., Cincinnati, OH (US); The General Hospital Corporation, Boston, MA (US)

(72) Inventors: Lee M. Kaplan, Wellesley, MA (US); Nicholas Stylopoulos, Swampscott, MA (US); Jason L. Harris, Lebanon, OH (US); Dwight Henninger, Waynesville, OH (US); Taylor W. Aronhalt, Loveland, OH (US); James W. Voegele, Cincinnati, OH (US)

(73) Assignees: Ethicon Endo-Surgery, Inc., Cincinnati, OH (US); The General Hospital Corporation, Boston, MA (US)

( * ) Notice: Subject to any disclaimer, the term of this patent is extended or adjusted under 35 U.S.C. 154(b) by 43 days.

(21) Appl. No.: 15/175,777

(22) Filed: Jun. 7, 2016

(65) Prior Publication Data
US 2017/0000827 A1    Jan. 5, 2017

Related U.S. Application Data

(62) Division of application No. 13/977,543, filed as application No. PCT/US2011/066358 on Dec. 21, 2011, now Pat. No. 9,381,219.

(60) Provisional application No. 61/427,968, filed on Dec. 29, 2010.

(51) Int. Cl.
| | | |
|---|---|---|
| A61K 35/35 | (2015.01) | |
| A61K 38/17 | (2006.01) | |
| C12N 7/00 | (2006.01) | |
| C12N 5/077 | (2010.01) | |
| C12N 15/86 | (2006.01) | |
| A61K 48/00 | (2006.01) | |
| C07K 14/705 | (2006.01) | |
| C07K 14/47 | (2006.01) | |
| C12N 15/85 | (2006.01) | |

(52) U.S. Cl.
CPC ............ *A61K 35/35* (2013.01); *A61K 38/177* (2013.01); *A61K 48/005* (2013.01); *C07K 14/47* (2013.01); *C07K 14/705* (2013.01); *C12N 5/0653* (2013.01); *C12N 7/00* (2013.01); *C12N 15/85* (2013.01); *C12N 15/86* (2013.01); *C12N 2506/1392* (2013.01); *C12N 2750/14143* (2013.01); *C12N 2799/025* (2013.01); *C12N 2830/002* (2013.01)

(58) Field of Classification Search
None
See application file for complete search history.

(56) References Cited

U.S. PATENT DOCUMENTS

| | | |
|---|---|---|
| 4,578,770 A | 3/1986 | Mitani |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 5,486,359 A | 1/1996 | Caplan et al. |
| 5,736,396 A | 4/1998 | Bruder et al. |
| 5,811,094 A | 9/1998 | Caplan et al. |
| 5,827,735 A | 10/1998 | Young et al. |
| 5,827,740 A | 10/1998 | Pittenger |
| 5,837,539 A | 11/1998 | Caplan et al. |
| 5,837,670 A | 11/1998 | Hartshorn |
| 5,843,723 A | 12/1998 | Dubensky, Jr. et al. |
| 2001/0032337 A1 | 10/2001 | Forman |
| 2004/0166061 A1 | 8/2004 | Enerback et al. |
| 2007/0022486 A1 | 1/2007 | Allen |

OTHER PUBLICATIONS

Bartlet et al., Brown adipose tissue activity controls triglyceride clearance. Nature Medicine. Feb. 2011;17(2):200-206.
Berkner et al. (1988) BioTechniques 6:616.
Boshart et al. (1985) Cell 41:521-530.
Bredenbeek, P. J., et al., J. Virol. (1993) 67: 6439-6446.
Capecchi (1980) Cell 22:479-488.
Cassiede P., et al., 30 J. Bone Miner. Res. (1996) 11(9): 1264-1273.
Cheneval et al., (1991) Proc. Natl. Acad. Sci. USA 88:8465-9.
Chu et al.. (1981) Gene 13:197.
Clark et al. J. Drug. Target 7, 269-83 (1999).
Davidson, B. L., et al., Nature Genetics (1993) 3: 219-223.
Davis et al. (1986) Basic Methods in Molecular Biology, Elsevier.
Douglas, J., et al., Nature Biotech. (1999) 17: 470-475.
Dull, T., et al., J. Virol. (1998) 72: 8463-8471.
Ekblom et al., Ann. N.Y. Acad. Sci., 857:194-211, 1998.
Felgner et al. (1987) Proc. Natl. Acad. Sci. USA 84:7413-7417.
Frolov, I., et al., Proc. Natl. Acad. Sci. USA (1996) 93: 11371-11377.
Graham et al. (1973) Virology, 52:456.

(Continued)

*Primary Examiner* — James D Schultz
(74) *Attorney, Agent, or Firm* — Mintz Levin Cohn Ferris Glovsky and Popeo, P.C.

(57) ABSTRACT

Methods and therapeutics are provided for treating metabolic disorders by increasing activation of brown adipose tissue. Generally, the methods and therapeutics can increase activation of brown adipose tissue to increase energy expenditure and induce weight loss. In one embodiment, a method for increasing activation of brown adipose tissue includes modifying brown adipocytes to express a gene that activates brown adipocytes, such as uncoupling protein 1. In another embodiment, a method for increasing brown adipose tissue activation includes increasing the number of brown adipocytes. This can be accomplished by inducing proliferation of adipocytes in vivo or expanding adipocytes ex vivo, transplanting adipocytes into brown adipose tissue depots or elsewhere and inducing differentiation of adipocyte progenitor cells, such as MSCs, adipocyte progenitor cells, preadipocytes and adipocyte precursor cells.

7 Claims, 3 Drawing Sheets

Specification includes a Sequence Listing.

(56) References Cited

OTHER PUBLICATIONS

Gronthos, S., Blood (1994) 84(12): 4164-4173.
International Preliminary Report on Patentability for Application No. PCT/US11/66358, dated Jul. 11, 2013 (8 pages).
International Search Report and Written Opinion for PCT Application No. PCT/US11/66358, dated Jul. 6, 2012 (14 pages).
Jaiswal, N., et al., J. Cell Biochem. (1997) 64(2): 295-312.
Johnstone, B., et al., (1998) 238(1): 265-272.
Kafri, T. etal., J. Virol. (1999) 73: 576-584.
Klein et al. (1987) Nature 327:70-73.
Ladner et al. (1987) EMBO J. 6:2693-2698.
Langin D. Recruitment of brown fat and conversion of white into brown adipocytes: strategies to fight the metabolic complications of obesity? Biochim Biophys Acta. Mar. 2010;1801(3):372-6.
Makino, S., etal., J. Clin. Invest. (1999) 103(5): 697-705.
Mannino et al. (1988) BioTechniques 6:682-690.
McKnight et al. (1984) Cell 37: 253-262.
Mochizuki, H., et al., J. Virol. (1998) 72: 8873-8883.
Molecular Biology of the Cell, 3rd Edition, ed. by Alberts et al., New York: Garland Publishing, 1994, Ch 19.
National Institute of Health,Clinical Guidelines on the Identification, Evaluation, and Treatment of Overweight and Obesity in Adults (1998).
Ng et al. (1985) Mol. Cell Bioi. 5: 2720-2732.
Rehnmark et al. in J Bioi Chem 265: 16464-16471. 1990.
Rosenfeld et al. (1991) Science 252:431-434.
Rosenfeld et al. (1992) Cell 68:143-155.
Sambrook et al. (1989) Molecular Cloning, a laboratory manual, Cold Spring Harbor Laboratories, N.Y.
Shigekawa et al. (1988) BioTechniques 6:742-751.
Sokolova et al., Evolution of mitochondrial uncoupling proteins: novel invertebrate UCP homologues suggest early evolutionary divergence of the UCP family. FEBS Lett. Jan. 17, 2005;579(2):313-7.
Sutton, R., et al., J. Virol. (1998) 72: 5781-5788.
Targeting of Retroviral Vectors for Gene Therapy, Hum. Gene Therapy (1993) 4: 129-141.
Wagner, E., et al., Proc. Natl. Acad. Sci. USA (1992)89: 6099-6103.
Xiong, C., et al., Science (1989) 243: 1188-1191.
Xu et al. (2001) Hum Gene Ther. 12:563-73.
Yoo, et al., J. Bone Joint Surg. Am. (1998) 80(12): 1745-1757.
Zhao et al. (2009) Reproduct. Bioi. Endocrin. 7: 37-45.

SEQUENCE LISTING

```
<160> NUMBER OF SEQ ID NOS: 15

<210> SEQ ID NO 1
<211> LENGTH: 1644
<212> TYPE: DNA
<213> ORGANISM: Homo sapiens

<400> SEQUENCE: 1
aagtgccggg caatctgggc ttaacgggtc ctccctgccc gagcaagagg aagggacgct      60
cacctttgag ctgctccaca gcgccgcctc tgcactggca ctacctagcc caggtggctc     120
tgcaggagtc cgaagtcgcg ggtttcgtgc ccgcatcagg caacagtgcc actgttgtct     180
tcagggctga gtcctttgt tcttgcactc acgcctctct gccctccaag ccaggatggt     240
gaacccgaca acttccgaag tgcaacccac catgggggtc aagatcttct cagccggagt     300
ttcagcttgc ctggcagata tcatcacctt cccgctggac actgccaaag tccgccttca     360
gatccaaggt gaaggccagg cttccagtac cattaggtat aaaggtgtcc tagggaccat     420
caccaccctg gcaaaaacag aaggattgcc gaaactgtac agcggtctgc ctgcgggcat     480
tcagaggcaa atcagctttg cctcactcag gattggcctc tacgactcag tccaagagta     540
cttctcttca gggagagaaa cacctgcctc tctcggaaac aagatctcag ccggcttaat     600
gactggaggt gtggcagtgt tcattgggca gcctacagag gtcgtgaagg tcagaatgca     660
agcccagagc catctgcatg ggatcaaacc ccgctacacg gggacctaca atgcttacag     720
agttatagcc accacagaaa gcttgtcaac actttggaaa gggacgaccc ctaatctaat     780
gagaaatgtc atcatcaatt gtacagagct ggtaacatat gacctcatga aggggccct     840 tgtaaacaac aaaatactgg cagatgacgt cccctgccat ttactgtcag ctcttgttgc     900
cgggttttgc accacactcc tggcctctcc agtggatgtg gtaaaaacaa gattcatcaa     960
ctctctgcca ggacagtacc caagcgtacc aagctgtgcg atgtccatgt acaccaagga    1020
aggaccgacg gccttttttca aagggttttgt ggcttctttt ctgcgactcg ggtcctgaa    1080 cgtcatcatg tttgtgtgct ttgaacagct gaaaaaagag ctgatgaagt ccagacagac    1140
agtggattgt accacataag caacttggag gaagagatac tgaacatcat tgggcttcta    1200
tgctgggaga ccacgaataa aaccaaccaa agaaatcaaa tgaacagctc cgttgactt    1260
```

-continued

```
atttacatta caagatcatt tccagtagag agttttgaaa cctcttttaa ttttttttaa    1320
agggaaaact aacacataca catagttttt attcttactg tcttaaagac agaagagcat    1380
agcattcact aatatttga gaaataata cctatataaa gtcctgtatt taactggtct     1440
ttggggagag gtgggagtgt atgactgggt ataaagaatt ctgattacag ctcaaactag    1500
tgggaaggaa aaattagtcc aaaacccttt acatcgataa acactttaaa aagaaagct    1560 atcaaaaaaa tattgccatt tcatcttatt tattgaccac agttcacagc taatatactc    1620
aataaagtat tgctaattcc atct                                           1644
```

<210> SEQ ID NO 2
<211> LENGTH: 307
<212> TYPE: PRT
<213> ORGANISM: Homo sapiens

<400> SEQUENCE: 2

```
Met Val Asn Pro Thr Thr Ser Glu Val Gln Pro Thr Met Gly Val Lys
1               5                   10                  15

Ile Phe Ser Ala Gly Val Ser Ala Cys Leu Ala Asp Ile Ile Thr Phe
            20                  25                  30

Pro Leu Asp Thr Ala Lys Val Arg Leu Gln Ile Gln Gly Glu Gly Gln
        35                  40                  45

Ala Ser Ser Thr Ile Arg Tyr Lys Gly Val Leu Gly Thr Ile Thr Thr
    50                  55                  60

Leu Ala Lys Thr Glu Gly Leu Pro Lys Leu Tyr Ser Gly Leu Pro Ala
65                  70                  75                  80

Gly Ile Gln Arg Gln Ile Ser Phe Ala Ser Leu Arg Ile Gly Leu Tyr
                85                  90                  95

Asp Ser Val Gln Glu Tyr Phe Ser Ser Gly Arg Glu Thr Pro Ala Ser
            100                 105                 110

Leu Gly Asn Lys Ile Ser Ala Gly Leu Met Thr Gly Gly Val Ala Val
        115                 120                 125

Phe Ile Gly Gln Pro Thr Glu Val Val Lys Val Arg Met Gln Ala Gln
    130                 135                 140

Ser His Leu His Gly Ile Lys Pro Arg Tyr Thr Gly Thr Tyr Asn Ala
145                 150                 155                 160

Tyr Arg Val Ile Ala Thr Thr Glu Ser Leu Ser Thr Leu Trp Lys Gly
                165                 170                 175

Thr Thr Pro Asn Leu Met Arg Asn Val Ile Ile Asn Cys Thr Glu Leu
            180                 185                 190

Val Thr Tyr Asp Leu Met Lys Gly Ala Leu Val Asn Asn Lys Ile Leu
        195                 200                 205

Ala Asp Asp Val Pro Cys His Leu Leu Ser Ala Leu Val Ala Gly Phe
    210                 215                 220

Cys Thr Thr Leu Leu Ala Ser Pro Val Asp Val Val Lys Thr Arg Phe
225                 230                 235                 240

Ile Asn Ser Leu Pro Gly Gln Tyr Pro Ser Val Pro Ser Cys Ala Met
                245                 250                 255

Ser Met Tyr Thr Lys Glu Gly Pro Thr Ala Phe Phe Lys Gly Phe Val
            260                 265                 270

Ala Ser Phe Leu Arg Leu Gly Ser Trp Asn Val Ile Met Phe Val Cys
        275                 280                 285

Phe Glu Gln Leu Lys Lys Glu Leu Met Lys Ser Arg Gln Thr Val Asp
    290                 295                 300
```

Cys Thr Thr
305

<210> SEQ ID NO 3
<211> LENGTH: 1646
<212> TYPE: DNA
<213> ORGANISM: Homo sapiens

<400> SEQUENCE: 3

| | |
|---|---|
| cactgcgaag cccagctgcg cgcgccttgg gattgactgt ccacgctcgc ccggctcgtc | 60 |
| cgacgcgccc tccgccagcc gacagacaca gccgcacgca ctgccgtgtt ctccctgcgg | 120 |
| ctcggacaca tagtatgacc attaggtgtt tcgtctccca cccatttttct atggaaaacc | 180 |
| aaggggatcg ggccatgata gccactggca gctttgaaga acgggacacc tttagagaag | 240 |
| cttgatcttg gaggcctcac cgtgagacct tacaaagccg gattccggca gagttcctct | 300 |
| atctcgtctt gttgctgatt aaaggtgccc ctgtctccag ttttttctcca tctcctggga | 360 |
| cgtagcagga atcagcatc atggttgggt tcaaggccac agatgtgccc cctactgcca | 420 |
| ctgtgaagtt tcttggggct ggcacagctg cctgcatcgc agatctcatc acctttcctc | 480 |
| tggatactgc taaagtccgg ttacagatcc aaggagaaag tcaggggcca gtgcgcgcta | 540 |
| cagccagcgc ccagtaccgc ggtgtgatgg gcaccattct gaccatggtg cgtactgagg | 600 |
| gcccccgaag cctctacaat gggctggttg ccggcctgca cgccaaatg agctttgcct | 660 |
| ctgtccgcat cggcctgtat gattctgtca acagttcta caccaagggc tctgagcatg | 720 |
| ccagcattgg gagccgcctc ctagcaggca gcaccacagg tgcccctggct gtggctgtgg | 780 |
| cccagcccac ggatgtggta aggtccgat tccaagctca ggcccgggct ggaggtggtc | 840 |
| ggagataacc aagcaccgtc aatgcctaca agaccattgc ccgagaggaa gggttccggg | 900 |
| gcctctggaa agggacctct cccaatgttg ctcgtaatgc cattgtcaac tgtgctgagc | 960 |
| tggtgaccta tgacctcatc aaggatgccc tcctgaaagc caacctcatg acagatgacc | 1020 |
| tcccttgcca cttcacttct gcctttgggg caggcttctg caccactgtc atcgcctccc | 1080 |
| ctgtagacgt ggtcaagacg agatacatga actctgccct gggccagtac agtagcgctg | 1140 |
| gccactgtgc ccttaccatg ctccagaagg agggccccg agccttctac aaagggttca | 1200 |
| tgccctcctt tctccgcttg ggttcctgga acgtggtgat gttcgtcacc tatgagcagc | 1260 |
| tgaaacgagc cctcatggct gcctgcactt cccgagaggc tcccttctga gcctctcctg | 1320 |
| ctgctgacct gatcacctct ggctttgtct ctagccgggc catgctttcc ttttcttcct | 1380 |
| tctttctctt ccctccttcc cttctctcct tccctctttc cccacctctt ccttccgctc | 1440 |
| ctttacctac caccttccct ctttctacat tctcatctac tcattgtctc agtgctggtg | 1500 |
| gagttgacat ttgacagtgt gggaggcctc gtaccagcca ggatcccaag cgtcccgtcc | 1560 |
| cttggaaagt tcagccagaa tcttcgtcct gcccccgaca gcccagccta gcccacttgt | 1620 |
| catccataaa gcaagctcaa ccttgg | 1646 |

<210> SEQ ID NO 4
<211> LENGTH: 309
<212> TYPE: PRT
<213> ORGANISM: Homo sapiens

<400> SEQUENCE: 4

Met Val Gly Phe Lys Ala Thr Asp Val Pro Pro Thr Ala Thr Val Lys
1               5                   10                  15

Phe Leu Gly Ala Gly Thr Ala Ala Cys Ile Ala Asp Leu Ile Thr Phe

```
                    20                  25                  30
Pro Leu Asp Thr Ala Lys Val Arg Leu Gln Ile Gln Gly Glu Ser Gln
            35                  40                  45

Gly Pro Val Arg Ala Thr Ala Ser Ala Gln Tyr Arg Gly Val Met Gly
        50                  55                  60

Thr Ile Leu Thr Met Val Arg Thr Glu Gly Pro Arg Ser Leu Tyr Asn
65                  70                  75                  80

Gly Leu Val Ala Gly Leu Gln Arg Gln Met Ser Phe Ala Ser Val Arg
                85                  90                  95

Ile Gly Leu Tyr Asp Ser Val Lys Gln Phe Tyr Thr Lys Gly Ser Glu
            100                 105                 110

His Ala Ser Ile Gly Ser Arg Leu Leu Ala Gly Ser Thr Thr Gly Ala
        115                 120                 125

Leu Ala Val Ala Val Ala Gln Pro Thr Asp Val Val Lys Val Arg Phe
    130                 135                 140

Gln Ala Gln Ala Arg Ala Gly Gly Gly Arg Arg Tyr Gln Ser Thr Val
145                 150                 155                 160

Asn Ala Tyr Lys Thr Ile Ala Arg Glu Glu Gly Phe Arg Gly Leu Trp
                165                 170                 175

Lys Gly Thr Ser Pro Asn Val Ala Arg Asn Ala Ile Val Asn Cys Ala
            180                 185                 190

Glu Leu Val Thr Tyr Asp Leu Ile Lys Asp Ala Leu Leu Lys Ala Asn
        195                 200                 205

Leu Met Thr Asp Asp Leu Pro Cys His Phe Thr Ser Ala Phe Gly Ala
    210                 215                 220

Gly Phe Cys Thr Thr Val Ile Ala Ser Pro Val Asp Val Val Lys Thr
225                 230                 235                 240

Arg Tyr Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
            260                 265                 270

Phe Met Pro Ser Phe Leu Arg Leu Gly Ser Trp Asn Val Val Met Phe
        275                 280                 285

Val Thr Tyr Glu Gln Leu Lys Arg Ala Leu Met Ala Ala Cys Thr Ser
    290                 295                 300

Arg Glu Ala Pro Phe
305

<210> SEQ ID NO 5
<211> LENGTH: 2438
<212> TYPE: DNA
<213> ORGANISM: Homo sapiens

<400> SEQUENCE: 5
gaaccagatc tggaactcac tcacctcccc tctcacctca ctgccctcac cagccagcct      60
cttgtcaagt gatcaggctg tcaaccaact tctctaggat aaggtttcag gtcagcccgt     120
gtgtataaga ccagtgccaa gccagaagca gcagagacaa cagtgaatga caaggagggg     180
ccatccaatc cctgctgcca cctcctggga tggagcccta gggagcccct gtgctgcccc     240
tgccgtggca ggactcacag ccccaccgct gcactgaagc ccagggctgt ggagcagcct     300
ctctccttgg acctcctctc ggccctaaag ggactgggca gagccttcca ggactatggt     360
tggactgaag ccttcagacg tgcctccac catggctgtg aagttcctgg gggcaggcac     420
agcagcctgt tttgctgacc tcgttacctt tccactggac acagccaagg tccgcctgca     480
```

```
gatccagggg gagaaccagg cggtccagac ggcccggctc gtgcagtacc gtggcgtgct    540
gggcaccatc ctgaccatgg tgcggactga ggtccctgc agcccctaca atgggctggt     600
ggccggcctg cagcgccaga tgagcttcgc ctccatccgc atcggcctct atgactccgt    660
caagcaggtg tacacccca aggcgcgga caactccagc ctcactaccc ggattttggc     720
cggctgcacc acaggagcca tggcggtgac ctgtgcccag cccacagatg tggtgaaggt    780
ccgatttcag gccagcatac acctcgggcc atccaggagc acagaaaat acagcgggac    840 tatggacgcc tacagaacca tcgccaggga ggaaggagtc aggggcctgt ggaaaggaac    900
tttgcccaac atcatgagga atgctatcgt caactgtgct gaggtggtga cctacgacat    960
cctcaaggag aagctgctgg actaccacct gctcactgac aacttcccct gccactttgt   1020
ctctgccttt ggagccggct ctgtgccac agtggtggcc tccccggtgg acgtggtgaa    1080
gacccggtat atgaactcac ctccaggcca gtacttcagc cccctcgact gtatgataaa    1140
gatggtggcc caggagggcc ccacagcctt ctacaaggga tttacaccct ccttttttgcg  1200 tttgggatcc tggaacgtgg tgatgttcgt aacctatgag cagctgaaac gggccctgat   1260
gaaagtccag atgttacggg aatcaccgtt tgaacaaga caagaaggcc actggtagct    1320
aacgtgtccg aaaccagtta agaatggaag aaaacggtgc atccacgcac acatggacac    1380
agacccacac atgtttacag aactgttgtt tacttgttgc tgattcaaga aacagaagta   1440
gaagaggagg agggattctg gtcttcactg ccatgcctca agaacaccctt tgttttgcac   1500 tgacaagatg gaaaataaat tatattaatt tttgaaaccc attaggcatg cctaatatatt  1560 aggcaagaga aaataaacca agatagatcc atttggacaa aatggaaggt tggagacgtg   1620
tatccccgtg aaatctggtt agataatgaa tgataagcag gaaggatggc aagcacggga   1680
cagggagggc ccacaatgga gtgggagatc agccacggag cctggaggga tgccacccag   1740
caacacagag ctggcgactg cagctgcacc atcacacatg catcatcagc ctatttgtaa   1800
tatgtctgcc acagagagtc cttttgggatt ctaggaaacc caaggaacaa gagaaaaaac   1860
tagagcctgt gctaaagaag ccctgctggg cccatgtgag gctggggctc gtaaatattc    1920
cctgacgaca ctgaagaatc aagagggcag ccccacttt cctacaaaat ggagggagcc    1980
atcccttccc tgtccacctc accaggggtg ctatgacatg caagtgagaa gctgggcatg   2040
aacgcacttt ataaaagcaa aagctctgtg taaatctaac tacaaggaca atgccttggg   2100
agagattttg tcgggacaga gaggagttgc cagggaagaa ggtttgaaag atacggttgt    2160
ctagaggtga gaccaaagga tccagagact tggggaccag aggtgacagt ggatgacgtg   2220
aagccacagg agccccaccc ccatgcagcc tcttccccac cccccccacc acgtgctcaa   2280
tcatgagtac ctcaaaggat tgttgggctt gggggaaaag aggtggattc ctgggcaaga   2340
acctaaagta gcaggactcg gaattctcgg gaaattatta tgactcaata aaagaattca   2400
caccttaggt gtgggagtaa gaacaaaaaa aaaaaaaa                          2438
```

<210> SEQ ID NO 6
<211> LENGTH: 312
<212> TYPE: PRT
<213> ORGANISM: Homo sapiens

<400> SEQUENCE: 6

Met Val Gly Leu Lys Pro Ser Asp Val Pro Pro Thr Met Ala Val Lys
1               5                   10                  15

Phe Leu Gly Ala Gly Thr Ala Ala Cys Phe Ala Asp Leu Val Thr Phe

|   |   |   | 20 |   |   |   | 25 |   |   |   | 30 |   |   |
|---|---|---|---|---|---|---|---|---|---|---|---|---|---|

Pro Leu Asp Thr Ala Lys Val Arg Leu Gln Ile Gln Gly Glu Asn Gln
        35                  40                  45

Ala Val Gln Thr Ala Arg Leu Val Gln Tyr Arg Gly Val Leu Gly Thr
 50                  55                  60

Ile Leu Thr Met Val Arg Thr Glu Gly Pro Cys Ser Pro Tyr Asn Gly
 65                  70                  75                  80

Leu Val Ala Gly Leu Gln Arg Gln Met Ser Phe Ala Ser Ile Arg Ile
                 85                  90                  95

Gly Leu Tyr Asp Ser Val Lys Gln Val Tyr Thr Pro Lys Gly Ala Asp
             100                 105                 110

Asn Ser Ser Leu Thr Thr Arg Ile Leu Ala Gly Cys Thr Thr Gly Ala
         115                 120                 125

Met Ala Val Thr Cys Ala Gln Pro Thr Asp Val Val Lys Val Arg Phe
     130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                 165                 170                 175

Gly Leu Trp Lys Gly Thr Leu Pro Asn Ile Met Arg Asn Ala Ile Val
             180                 185                 190

Asn Cys Ala Glu Val Val Thr Tyr Asp Ile Leu Lys Glu Lys Leu Leu
         195                 200                 205

Asp Tyr His Leu Leu Thr Asp Asn Phe Pro Cys His Phe Val Ser Ala
     210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                 245                 250                 255

Leu Asp Cys Met Ile Lys Met Val Ala Gln Glu Gly Pro Thr Ala Phe
             260                 265                 270

Tyr Lys Gly Phe Thr Pro Ser Phe Leu Arg Leu Gly Ser Trp Asn Val
         275                 280                 285

Val Met Phe Val Thr Tyr Glu Gln Leu Lys Arg Ala Leu Met Lys Val
     290                 295                 300

Gln Met Leu Arg Glu Ser Pro Phe
305                 310

<210> SEQ ID NO 7
<211> LENGTH: 2959
<212> TYPE: DNA
<213> ORGANISM: Homo sapiens

<400> SEQUENCE: 7
actacattgc ccagtaacct cctgggctcc gctgtgtttt tctattctgg ggtgtaaggg    60
gcagctggac cactccagct gggactgcta ggaaggttgc gggtccaccc ggccgagccg   120
aacgagggaa atggtcctca cccggccact cgccggttga aaaggggccg ccctggcagg   180
gaagcggccg ccgcggcgcg gtgcagcgca gcggcgagaa ggagtgcgtt atcgtcttgc   240
gctactgctg aatgtccgtc ccggaggagg aggagaggct tttgccgctg acccagagat   300
ggccccgagc gagcaaattc ctactgtccg gctgcgcggc taccgtggcc gagctagcaa   360 cctttccccct ggatctcaca aaaactcgac tccaaatgca aggagaagca gctcttgctc   420
ggttgggaga cggtgcaaga gaatctgccc cctatagggg aatggtgcgc acagccctag   480

```
ggatcattga agaggaaggc tttctaaagc tttggcaagg agtgacaccc gccatttaca      540
gacacgtagt gtattctgga ggtcgaatgg tcacatatga acatctccga gaggttgtgt      600
ttggcaaaag tgaagatgag cattatcccc tttggaaatc agtcattgga gggatgatgg      660
ctggtgttat tggccagttt ttagccaatc caactgacct agtgaaggtt cagatgcaaa      720
tggaaggaaa aaggaaactg aaggaaaaac cattgcgatt tcgtggtgta catcatgcat      780
ttgcaaaaat cttagctgaa ggaggaatac gagggctttg gcaggctggg gtacccaata      840
tacaaagagc agcactggtg aatatgggag atttaaccac ttatgataca gtgaaacact      900
acttggtatt gaatacacca cttgaggaca atatcatgac tcacggttta tcaagtttat      960
gttctggact ggtagcttct attctgggaa caccagccga tgtcatcaaa agcagaataa     1020
tgaatcaacc acgagataaa caaggaaggg acttttgta taaatcatcg actgactgct     1080
tgattcaggc tgttcaaggt gaaggattca tgagtctata taaaggcttt ttaccatctt     1140
ggctgagaat gaccccttgg tcaatggtgt tctggcttac ttatgaaaaa atcagagaga     1200
tgagtggagt cagtccattt taaaccccta agatgcaacc cttaaagat acagtgttca      1260 gtattattga aatatgggca tctgcaacac atacccccta ttatttctac ctctttagga     1320
agacacctat tccacagaga ctgatttata gggggcagca ctttattttt ttctggaaac     1380
ccaagttctc tttgactcct cttttttgtcc aaaagtgatc tggtcggatc tcacaaggcc    1440
atccaatgag accccgcaca gcattttcta agaagaatc gaagcctgac cactttcacc     1500
ttgggcaaga aggtttggcc tttgagttgc tattctatgc tgaagagcct gcttagagga     1560
ggagtaccag gagggagcca gcatttcaga tctgaagtag acgataggaa tgtggaagaa     1620
cacatacata gtgcttaaga aatacattta acctgttatg tcagtattta tcaatgaagt     1680
ttgataattc acttttctgt cattgttaaa gcgtacatac tgtaaattaa agggaggtga     1740
atggaaatta atgaataaac attttgagtt tccctagtgt tgaaggaagg tgtacttttt     1800
cttgtcagaa agataaaaaa aatcaagttg agatgatgtt tgaatttcaa gaaagaggc     1860 tgctttctgt cagtgccctc tcattagatc tgtgttaatt agttagcact ccactgcaca     1920
tgctaatgac ttcctctgac agccacacac cgaatcttga tgaaaaaga gaagagcatt     1980 tgccttgtta catagtctgt tacaagccag atatgttgct agctctcaag agttgtaata     2040
tattaagaac tacaacttat ttgattaaaa ctcagctgta tagatccttt tataaagcac     2100
cttttgttaa acatcagcct ttcattggta ttttaaaagc aaggcagata gatatgaagt     2160
cagccaactc tgacatgcgt cctttcttat ctcccttacc tgacactagg ggctctagag     2220
aggcagagag agcactcaca aatcacacta aaactgccag cggcctgact cttactcagt     2280
ttagcaaaaa ttcttgccta aaaagtgata agtaaaaatc tgtttatggt atacagttat     2340
gtctcgaatc tttgaatcaa atccatgttc ttattttaga aaggtaagag ttcttcaaat     2400
tcagctacat accaccggct ctcccaacct cagacggtgg gcatttctgg atggatggct     2460
gcggttatgg ataaaggctg taactgttaa cacagaaaaa catgaaaagc tcaggcccaa     2520
gaaaggcctt ggagccagcc aaacagaatt tgttctaatg gacatggatg atgttgaaca     2580
gaaaaaagtt tacaagtgct tgtggttgc actaatgtat actcactgcc attttaagag      2640
ggggaagtac attttaaaat atatttgaat gtcatgtact gatatgcagt agcttattgt     2700
ttttctagtt gcagagaatg tgaagtttaa tctcttaaaa tatttagatg gtctactttt      2760
tcattgaatt tgtcaatatg taattgcgtt gtaaaatatt atatatatat atatatatat     2820
```

```
atatatatat atatgcttaa cttcccaagt gttctgcatt gaaccactta gggaaaattt    2880
tgtttgtttt tatgttttgt aattttttaaa attaagtaaa gactggatca aaataattgc    2940
atccaacctg gaccgtgaa                                                  2959
```

```
<210> SEQ ID NO 8
<211> LENGTH: 323
<212> TYPE: PRT
<213> ORGANISM: Homo sapiens

<400> SEQUENCE: 8
```

Met Ser Val Pro Glu Glu Glu Arg Leu Leu Pro Leu Thr Gln Arg
1               5                   10                  15

Trp Pro Arg Ala Ser Lys Phe Leu Leu Ser Gly Cys Ala Ala Thr Val
                20                  25                  30

Ala Glu Leu Ala Thr Phe Pro Leu Asp Leu Thr Lys Thr Arg Leu Gln
                35                  40                  45

Met Gln Gly Glu Ala Ala Leu Ala Arg Leu Gly Asp Gly Ala Arg Glu
    50                  55                  60

Ser Ala Pro Tyr Arg Gly Met Val Arg Thr Ala Leu Gly Ile Ile Glu
65              70                  75                  80

Glu Glu Gly Phe Leu Lys Leu Trp Gln Gly Val Thr Pro Ala Ile Tyr
                85                  90                  95

Arg His Val Val Tyr Ser Gly Gly Arg Met Val Thr Tyr Glu His Leu
                100                 105                 110

Arg Glu Val Val Phe Gly Lys Ser Glu Asp Glu His Tyr Pro Leu Trp
                115                 120                 125

Lys Ser Val Ile Gly Gly Met Met Ala Gly Val Ile Gly Gln Phe Leu
    130                 135                 140

Ala Asn Pro Thr Asp Leu Val Lys Val Gln Met Gln Met Glu Gly Lys
145                 150                 155                 160

Arg Lys Leu Glu Gly Lys Pro Leu Arg Phe Arg Gly Val His His Ala
                165                 170                 175

Phe Ala Lys Ile Leu Ala Glu Gly Gly Ile Arg Gly Leu Trp Ala Gly
                180                 185                 190

Trp Val Pro Asn Ile Gln Arg Ala Ala Leu Val Asn Met Gly Asp Leu
            195                 200                 205

Thr Thr Tyr Asp Thr Val Lys His Tyr Leu Val Leu Asn Thr Pro Leu
    210                 215                 220

Glu Asp Asn Ile Met Thr His Gly Leu Ser Ser Leu Cys Ser Gly Leu
225                 230                 235                 240

Val Ala Ser Ile Leu Gly Thr Pro Ala Asp Val Ile Lys Ser Arg Ile
                245                 250                 255

Met Asn Gln Pro Arg Asp Lys Gln Gly Arg Gly Leu Leu Tyr Lys Ser
                260                 265                 270

Ser Thr Asp Cys Leu Ile Gln Ala Val Gln Gly Glu Gly Phe Met Ser
            275                 280                 285

Leu Tyr Lys Gly Phe Leu Pro Ser Trp Leu Arg Met Thr Pro Trp Ser
    290                 295                 300

Met Val Phe Trp Leu Thr Tyr Glu Lys Ile Arg Glu Met Ser Gly Val
305                 310                 315                 320

Ser Pro Phe

```
<210> SEQ ID NO 9
<211> LENGTH: 1601
```

```
<212> TYPE: DNA
<213> ORGANISM: Homo sapiens

<400> SEQUENCE: 9
gcttaacggt cctctggtct ctctctcccc tcagctgagt cccttccctg tctttcactc      60
ttctggcatc ggtggtttta cttcttcgat tgaaccctgc ttcctcgacc ccctgggag     120
gccgccttct tcaggcgcct cccttctctc cacgagctcg ctctgacagc tgaggaactg    180
gcaagatcct gctacccaga gggtgaatgg gtatctttcc cggaataatc ctaatttttc    240
taagggtgaa gtttgcaacg gcggccgtga ttgtaagcgg acaccagaaa agtaccactg    300
taagtcatga gatgtctggt ctgaattgga aacccttgt atatggcggc cttgcctcta    360
tcgtggctga gtttgggact ttccctgtgg accttaccaa aacacgactt caggttcaag    420
gccaaagcat tgatgcccgt ttcaaagaga taaaatatag agggatgttc catgcgctgt    480
ttcgcatctg taaagaggaa ggtgtattgg ctctctattc aggaattgct cctgcgttgc    540
taagacaagc atcatatggc accattaaaa ttgggattta ccaaagcttg aagcgcttat    600
tcgtagaacg tttagaagat gaaactcttt taattaatat gatctgtggg gtagtgtcag    660
gagtgatatc ttccactata gccaatccca ccgatgttct aaagattcga atgcaggctc    720
aaggaagctt gttccaaggg agcatgattg gaagctttat cgatatatac aacaagaag    780
gcaccagggg tctgtggagg ggtgtggttc caactgctca gcgtgctgcc atcgttgtag    840
gagtagagct accagtctat gatattacta agaagcattt aatattgtca ggaatgatgg    900
gcgatacaat tttaactcac ttcgtttcca gctttacatg tggtttggct ggggctctgg    960
cctccaaccc ggttgatgtg gttcgaactc gcatgatgaa ccagagggca atcgtgggac   1020
atgtggatct ctataagggc actgttgatg gtatttttaaa gatgtggaaa catgagggct   1080
tttttgcact ctataaagga ttttggccaa actggcttcg gcttggaccc tggaacatca   1140
tttttttat tacatacgag cagctaaaga ggcttcaaat ctaagaactg aattatatgt    1200
gagcccagcc ctgccagcct ttctactcct ttgcccttt cccgtgttct aatgtatttt    1260
gacaatgttg taagtgttta ccaagccgtt ggtctcctaa gggcctcctg atggaagaac    1320
agtggggtgg ttcaaagtta tttctatgtt tgtgttacca tgttaacttt tccccgagag    1380
aaagtgttaa cattgagact ctggccccag attggtatct tctatgaaga tggatactga    1440
tgggtgacat tgaaaacggc ctgctttcca aatgtggtta aatgtaattg gttagcccca    1500
gacttgggct agagcagaag gcataggcca gggtggttat tgctatatgt gttacagacc    1560
tcggttctca ttaaagtatt tattggcaga atcacaaaaa a                        1601

<210> SEQ ID NO 10
<211> LENGTH: 325
<212> TYPE: PRT
<213> ORGANISM: Homo sapiens

<400> SEQUENCE: 10

Met Gly Ile Phe Pro Gly Ile Ile Leu Ile Phe Leu Arg Val Lys Phe
1               5                   10                  15

Ala Thr Ala Ala Val Ile Val Ser Gly His Gln Lys Ser Thr Thr Val
            20                  25                  30

Ser His Glu Met Ser Gly Leu Asn Trp Lys Pro Phe Val Tyr Gly Gly
        35                  40                  45

Leu Ala Ser Ile Val Ala Glu Phe Gly Thr Phe Pro Val Asp Leu Thr
    50                  55                  60
```

```
Lys Thr Arg Leu Gln Val Gln Gly Gln Ser Ile Asp Ala Arg Phe Lys
 65                  70                  75                  80

Glu Ile Lys Tyr Arg Gly Met Phe His Ala Leu Phe Arg Ile Cys Lys
                 85                  90                  95

Glu Glu Gly Val Leu Ala Leu Tyr Ser Gly Ile Ala Pro Ala Leu Leu
            100                 105                 110

Arg Gln Ala Ser Tyr Gly Thr Ile Lys Ile Gly Ile Tyr Gln Ser Leu
        115                 120                 125

Lys Arg Leu Phe Val Glu Arg Leu Glu Asp Glu Thr Leu Leu Ile Asn
130                 135                 140

Met Ile Cys Gly Val Val Ser Gly Val Ile Ser Ser Thr Ile Ala Asn
145                 150                 155                 160

Pro Thr Asp Val Leu Lys Ile Arg Met Gln Ala Gln Gly Ser Leu Phe
                165                 170                 175

Gln Gly Ser Met Ile Gly Ser Phe Ile Asp Ile Tyr Gln Gln Glu Gly
            180                 185                 190

Thr Arg Gly Leu Trp Arg Gly Val Val Pro Thr Ala Gln Arg Ala Ala
        195                 200                 205

Ile Val Val Gly Val Glu Leu Pro Val Tyr Asp Ile Thr Lys Lys His
210                 215                 220

Leu Ile Leu Ser Gly Met Met Gly Asp Thr Ile Leu Thr His Phe Val
225                 230                 235                 240

Ser Ser Phe Thr Cys Gly Leu Ala Gly Ala Leu Ala Ser Asn Pro Val
                245                 250                 255

Asp Val Val Arg Thr Arg Met Met Asn Gln Arg Ala Ile Val Gly His
            260                 265                 270

Val Asp Leu Tyr Lys Gly Thr Val Asp Gly Ile Leu Lys Met Trp Lys
        275                 280                 285

His Glu Gly Phe Phe Ala Leu Tyr Lys Gly Phe Trp Pro Asn Trp Leu
290                 295                 300

Arg Leu Gly Pro Trp Asn Ile Ile Phe Phe Ile Thr Tyr Glu Gln Leu
305                 310                 315                 320

Lys Arg Leu Gln Ile
                325

<210> SEQ ID NO 11
<211> LENGTH: 477
<212> TYPE: PRT
<213> ORGANISM: Homo sapiens

<400> SEQUENCE: 11

Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
        35                  40                  45

Ser Pro Glu Pro Leu Ser Gln Gln Trp Thr Ala Gly Met Gly Leu Leu
    50                  55                  60

Met Ala Leu Ile Val Leu Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110
```

```
Pro Phe Gly Ala Thr Ile Val Val Trp Gly Arg Trp Glu Tyr Gly Ser
        115                 120                 125
Phe Phe Cys Glu Leu Trp Thr Ser Val Asp Val Leu Cys Val Thr Ala
130                 135                 140
Ser Ile Glu Thr Leu Cys Val Ile Ala Leu Asp Arg Tyr Leu Ala Ile
145                 150                 155                 160
Thr Ser Pro Phe Arg Tyr Gln Ser Leu Leu Thr Arg Ala Arg Ala Arg
                165                 170                 175
Gly Leu Val Cys Thr Val Trp Ala Ile Ser Ala Leu Val Ser Phe Leu
                180                 185                 190
Pro Ile Leu Met His Trp Trp Arg Ala Glu Ser Asp Glu Ala Arg Arg
        195                 200                 205
Cys Tyr Asn Asp Pro Lys Cys Cys Asp Phe Val Thr Asn Arg Ala Tyr
210                 215                 220
Ala Ile Ala Ser Ser Val Val Ser Phe Tyr Val Pro Leu Cys Ile Met
225                 230                 235                 240
Ala Phe Val Tyr Leu Arg Val Phe Arg Glu Ala Gln Lys Gln Val Lys
                245                 250                 255
Lys Ile Asp Ser Cys Glu Arg Arg Phe Leu Gly Gly Pro Ala Arg Pro
                260                 265                 270
Pro Ser Pro Ser Pro Ser Pro Val Pro Ala Pro Ala Pro Pro Pro Gly
        275                 280                 285
Pro Pro Arg Pro Ala Ala Ala Ala Thr Ala Pro Leu Ala Asn Gly
        290                 295                 300
Arg Ala Gly Lys Arg Arg Pro Ser Arg Leu Val Ala Leu Arg Glu Gln
305                 310                 315                 320
Lys Ala Leu Lys Thr Leu Gly Ile Ile Met Gly Val Phe Thr Leu Cys
                325                 330                 335
Trp Leu Pro Phe Phe Leu Ala Asn Val Val Lys Ala Phe His Arg Glu
                340                 345                 350
Leu Val Pro Asp Arg Leu Phe Val Phe Phe Asn Trp Leu Gly Tyr Ala
        355                 360                 365
Asn Ser Ala Phe Asn Pro Ile Ile Tyr Cys Arg Ser Pro Asp Phe Arg
        370                 375                 380
Lys Ala Phe Gln Gly Leu Leu Cys Cys Ala Arg Arg Ala Ala Arg Arg
385                 390                 395                 400
Arg His Ala Thr His Gly Asp Arg Pro Arg Ala Ser Gly Cys Leu Ala
                405                 410                 415
Arg Pro Gly Pro Pro Ser Pro Gly Ala Ala Ser Asp Asp Asp Asp
                420                 425                 430
Asp Asp Val Val Gly Ala Thr Pro Pro Ala Arg Leu Leu Glu Pro Trp
        435                 440                 445
Ala Gly Cys Asn Gly Gly Ala Ala Ala Asp Ser Asp Ser Ser Leu Asp
        450                 455                 460
Glu Pro Cys Arg Pro Gly Phe Ala Ser Glu Ser Lys Val
465                 470                 475
```

<210> SEQ ID NO 12
<211> LENGTH: 426
<212> TYPE: PRT
<213> ORGANISM: Homo sapiens

<400> SEQUENCE: 12

Met Glu Ala Ala Val Ala Ala Pro Arg Pro Arg Leu Leu Leu Leu Val

-continued

```
1               5                   10                  15
Leu Ala Ala Ala Ala Ala Ala Ala Leu Leu Pro Gly Ala Thr
                20                  25              30
Ala Leu Gln Cys Phe Cys His Leu Cys Thr Lys Asp Asn Phe Thr Cys
            35              40              45
Val Thr Asp Gly Leu Cys Phe Val Ser Val Thr Glu Thr Thr Asp Lys
        50              55              60
Val Ile His Asn Ser Met Cys Ile Ala Glu Ile Asp Leu Ile Pro Arg
65              70              75              80
Asp Arg Pro Phe Val Cys Ala Pro Ser Ser Lys Thr Gly Ser Val Thr
                85              90              95
Thr Thr Tyr Cys Cys Asn Gln Asp His Cys Asn Lys Ile Glu Leu Pro
            100             105             110
Thr Thr Gly Leu Pro Leu Leu Val Gln Arg Thr Ile Ala Arg Thr Ile
        115             120             125
Val Leu Gln Glu Ser Ile Gly Lys Gly Arg Phe Gly Glu Val Trp Arg
    130             135             140
Gly Lys Trp Arg Gly Glu Val Ala Val Lys Ile Phe Ser Ser Arg
145             150             155             160
Glu Glu Arg Ser Trp Phe Arg Glu Ala Glu Ile Tyr Gln Thr Val Met
                165             170             175
Leu Arg His Glu Asn Ile Leu Gly Phe Ile Ala Ala Asp Asn Lys Asp
            180             185             190
Asn Gly Thr Trp Thr Gln Leu Trp Leu Val Ser Asp Tyr His Glu His
        195             200             205
Gly Ser Leu Phe Asp Tyr Leu Asn Arg Tyr Thr Val Thr Val Glu Gly
    210             215             220
Met Ile Lys Leu Ala Leu Ser Thr Ala Ser Gly Leu Ala His Leu His
225             230             235             240
Met Glu Ile Val Gly Thr Gln Gly Lys Pro Ala Ile Ala His Arg Asp
                245             250             255
Leu Lys Ser Lys Asn Ile Leu Val Lys Lys Asn Gly Thr Cys Cys Ile
            260             265             270
Ala Asp Leu Gly Leu Ala Val Arg His Asp Ser Ala Thr Asp Thr Ile
        275             280             285
Asp Ile Ala Pro Asn His Arg Val Gly Thr Lys Arg Tyr Met Ala Pro
    290             295             300
Glu Val Leu Asp Asp Ser Ile Asn Met Lys His Phe Glu Ser Phe Lys
305             310             315             320
Arg Ala Asp Ile Tyr Ala Met Gly Leu Val Phe Trp Glu Ile Ala Arg
                325             330             335
Arg Cys Ser Ile Gly Gly Ile His Glu Asp Tyr Gln Leu Pro Tyr Tyr
            340             345             350
Asp Leu Val Pro Ser Asp Pro Ser Val Glu Glu Met Arg Lys Val Val
        355             360             365
Cys Glu Gln Lys Leu Arg Pro Asn Ile Pro Asn Arg Trp Gln Ser Cys
    370             375             380
Glu Ala Leu Arg Val Met Ala Lys Ile Met Arg Glu Cys Trp Tyr Ala
385             390             395             400
Asn Gly Ala Ala Arg Leu Thr Ala Leu Arg Ile Lys Lys Thr Leu Ser
                405             410             415
Gln Leu Ser Gln Gln Glu Gly Ile Lys Met
            420             425
```

<210> SEQ ID NO 13
<211> LENGTH: 300
<212> TYPE: PRT
<213> ORGANISM: Homo sapiens

<400> SEQUENCE: 13

```
Met Asp Leu Pro Pro Gln Leu Ser Phe Gly Leu Tyr Val Ala Ala Phe
1               5                   10                  15

Ala Leu Gly Phe Pro Leu Asn Val Leu Ala Ile Arg Gly Ala Thr Ala
            20                  25                  30

His Ala Arg Leu Arg Leu Thr Pro Ser Leu Val Tyr Ala Leu Asn Leu
        35                  40                  45

Gly Cys Ser Asp Leu Leu Leu Thr Val Ser Leu Pro Leu Lys Ala Val
    50                  55                  60

Glu Ala Leu Ala Ser Gly Ala Trp Pro Leu Pro Ala Ser Leu Cys Pro
65                  70                  75                  80

Val Phe Ala Val Ala His Phe Phe Pro Leu Tyr Ala Gly Gly Gly Phe
                85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

Ala Ile Trp Ala Leu Val Leu Cys His Leu Gly Leu Val Phe Gly Leu
    130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Phe Phe
            180                 185                 190

Leu Pro Leu Ala Ile Thr Ala Phe Cys Tyr Val Gly Cys Leu Arg Ala
        195                 200                 205

Leu Ala Arg Ser Gly Leu Thr His Arg Arg Lys Leu Arg Ala Ala Trp
    210                 215                 220

Val Ala Gly Gly Ala Leu Leu Thr Leu Leu Cys Val Gly Pro Tyr
225                 230                 235                 240

Asn Ala Ser Asn Val Ala Ser Phe Leu Tyr Pro Asn Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
        275                 280                 285

Cys Ala Ala Arg Thr Gln Gly Gly Lys Ser Gln Lys
    290                 295                 300
```

<210> SEQ ID NO 14
<211> LENGTH: 330
<212> TYPE: PRT
<213> ORGANISM: Homo sapiens

<400> SEQUENCE: 14

```
Met Leu Pro Asp Trp Lys Ser Ser Leu Ile Leu Met Ala Tyr Ile Ile
1               5                   10                  15

Ile Phe Leu Thr Gly Leu Pro Ala Asn Leu Leu Ala Leu Arg Ala Phe
            20                  25                  30
```

```
Val Gly Arg Ile Arg Gln Pro Gln Pro Ala Pro Val His Ile Leu Leu
            35                  40                  45

Leu Ser Leu Thr Leu Ala Asp Leu Leu Leu Leu Leu Leu Pro Phe
 50                  55                  60

Lys Ile Ile Glu Ala Ala Ser Asn Phe Arg Trp Tyr Leu Pro Lys Val
 65                  70                  75                  80

Val Cys Ala Leu Thr Ser Phe Gly Phe Tyr Ser Ser Ile Tyr Cys Ser
                 85                  90                  95

Thr Trp Leu Leu Ala Gly Ile Ser Ile Glu Arg Tyr Leu Gly Val Ala
            100                 105                 110

Phe Pro Val Gln Tyr Lys Leu Ser Arg Arg Pro Leu Tyr Gly Val Ile
            115                 120                 125

Ala Ala Leu Val Ala Trp Val Met Ser Phe Gly His Cys Thr Ile Val
        130                 135                 140

Ile Ile Val Gln Tyr Leu Asn Thr Thr Glu Gln Val Arg Ser Gly Asn
145                 150                 155                 160

Glu Ile Thr Cys Tyr Glu Asn Phe Thr Asp Asn Gln Leu Asp Val Val
                165                 170                 175

Leu Pro Val Arg Leu Glu Leu Cys Leu Val Leu Phe Phe Ile Pro Met
            180                 185                 190

Ala Val Thr Ile Phe Cys Tyr Trp Arg Phe Val Trp Ile Met Leu Ser
        195                 200                 205

Gln Pro Leu Val Gly Ala Gln Arg Arg Arg Arg Ala Val Gly Leu Ala
    210                 215                 220

Val Val Thr Leu Leu Asn Phe Leu Val Cys Phe Gly Pro Tyr Asn Val
225                 230                 235                 240

Ser His Leu Val Gly Tyr His Gln Arg Lys Ser Pro Trp Trp Arg Ser
                245                 250                 255

Ile Ala Val Val Phe Ser Ser Leu Asn Ala Ser Leu Asp Pro Leu Leu
            260                 265                 270

Phe Tyr Phe Ser Ser Ser Val Val Arg Arg Ala Phe Gly Arg Gly Leu
        275                 280                 285

Gln Val Leu Arg Asn Gln Gly Ser Ser Leu Leu Gly Arg Arg Gly Lys
    290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330

<210> SEQ ID NO 15
<211> LENGTH: 860
<212> TYPE: PRT
<213> ORGANISM: Homo sapiens

<400> SEQUENCE: 15

Met Gly Pro Trp Gly Trp Lys Leu Arg Trp Thr Val Ala Leu Leu Leu
  1               5                  10                  15

Ala Ala Ala Gly Thr Ala Val Gly Asp Arg Cys Glu Arg Asn Glu Phe
             20                  25                  30

Gln Cys Gln Asp Gly Lys Cys Ile Ser Tyr Lys Trp Val Cys Asp Gly
             35                  40                  45

Ser Ala Glu Cys Gln Asp Gly Ser Asp Glu Ser Gln Glu Thr Cys Leu
         50                  55                  60

Ser Val Thr Cys Lys Ser Gly Asp Phe Ser Cys Gly Gly Arg Val Asn
```

```
            65                  70                  75                  80
Arg Cys Ile Pro Gln Phe Trp Arg Cys Asp Gly Gln Val Asp Cys Asp
                    85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
            115                 120                 125

Asp Ser Asp Arg Asp Cys Leu Asp Gly Ser Asp Glu Ala Ser Cys Pro
130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                    165                 170                 175

Ser Asp Glu Trp Pro Gln Arg Cys Arg Gly Leu Tyr Val Phe Gln Gly
                    180                 185                 190

Asp Ser Ser Pro Cys Ser Ala Phe Glu Phe His Cys Leu Ser Gly Glu
            195                 200                 205

Cys Ile His Ser Ser Trp Arg Cys Asp Gly Gly Pro Asp Cys Lys Asp
            210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                    245                 250                 255

Arg Glu Tyr Asp Cys Lys Asp Met Ser Asp Glu Val Gly Cys Val Asn
                    260                 265                 270

Val Thr Leu Cys Glu Gly Pro Asn Lys Phe Lys Cys His Ser Gly Glu
            275                 280                 285

Cys Ile Thr Leu Asp Lys Val Cys Asn Met Ala Arg Asp Cys Arg Asp
            290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                    325                 330                 335

Glu Cys Leu Cys Pro Asp Gly Phe Gln Leu Val Ala Gln Arg Arg Cys
                    340                 345                 350

Glu Asp Ile Asp Glu Cys Gln Asp Pro Asp Thr Cys Ser Gln Leu Cys
            355                 360                 365

Val Asn Leu Glu Gly Gly Tyr Lys Cys Gln Cys Glu Glu Gly Phe Gln
370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                    405                 410                 415

Ser Glu Tyr Thr Ser Leu Ile Pro Asn Leu Arg Asn Val Val Ala Leu
                    420                 425                 430

Asp Thr Glu Val Ala Ser Asn Arg Ile Tyr Trp Ser Asp Leu Ser Gln
            435                 440                 445

Arg Met Ile Cys Ser Thr Gln Leu Asp Arg Ala His Gly Val Ser Ser
            450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                    485                 490                 495
```

-continued

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
            515                 520                 525

Gly Phe Met Tyr Trp Thr Asp Trp Gly Thr Pro Ala Lys Ile Lys Lys
            530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
            595                 600                 605

Phe Ser Leu Ala Val Phe Glu Asp Lys Val Phe Trp Thr Asp Ile Ile
            610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
                660                 665                 670

Ser Asn Gly Gly Cys Gln Tyr Leu Cys Leu Pro Ala Pro Gln Ile Asn
            675                 680                 685

Pro His Ser Pro Lys Phe Thr Cys Ala Cys Pro Asp Gly Met Leu Leu
            690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
                740                 745                 750

Pro Gly Ala Thr Pro Gly Leu Thr Thr Val Glu Ile Val Thr Met Ser
            755                 760                 765

His Gln Ala Leu Gly Asp Val Ala Gly Arg Gly Asn Glu Lys Lys Pro
770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
            835                 840                 845

Ser Arg Gln Met Val Ser Leu Glu Asp Asp Val Ala
            850                 855                 860

BROWN ADIPOCYTE MODIFICATION

CROSS REFERENCE TO RELATED APPLICATIONS

The present application is a divisional of U.S. patent application Ser. No. 13/977,543 entitled "Brown Adipocyte Modification" filed on Mar. 3, 2014, which is a U.S. national stage filing under 35 U.S.C. § 371 of International Application No. PCT/US11/66358 entitled "Brown Adipocyte Modification" filed on Dec. 21, 2011, which claims priority to U.S. Provisional Patent Application Ser. No. 61/427,968 entitled "Brown Adipocyte Modification" filed on Dec. 29, 2010, which are hereby incorporated by reference herein in their entireties.

FIELD OF THE INVENTION

The present invention relates to methods and compositions for the treatment of metabolic disease.

BACKGROUND OF THE INVENTION

Obesity represents the most prevalent of body weight disorders, and it is the most important nutritional disorder in the Western world, with estimates of its prevalence ranging from 30% to 50% of the middle-aged population. The number of overweight and obese Americans has continued to increase since 1960, a trend that is not slowing down. Today, 64.5 percent of adult Americans (about 127 million) are categorized as being overweight or obese. Obesity is becoming a growing concern as the number of people with obesity continues to increase and more is learned about: the negative health effects of obesity. Each year, obesity causes at least 300,000 deaths in the U.S., and healthcare costs of American adults with obesity amount to more than $125 billion (American Obesity Association). Severe obesity, in which a person is 100 pounds or more over ideal body weight, in particular poses significant risks for severe health problems. Accordingly, a great deal of attention is being focused on treating patients with obesity.

Even mild obesity increases the risk for premature death, diabetes, hypertension, atherosclerosis, gallbladder disease and certain types of cancer. Because of its high prevalence and significant health consequences, its treatment should be a high public health priority. Therefore, a better understanding of the mechanism for weight loss is needed. Moreover, a need exists for better methods and therapeutics for treating obesity and inducing weight loss.

SUMMARY OF THE INVENTION

The present invention generally provides methods and compositions for treating metabolic disorders involving activation of brown adipose tissue. One aspect of the invention discloses methods and compositions for modifying brown adipose tissue to treat obesity by altering at least one brown adipocyte by expressing a vector capable of modulating uncoupling protein activity, where modulating the uncoupling protein signaling alters adipocyte activation. Another aspect of the invention discloses methods and compositions for augmenting brown adipose tissue in a subject by providing a population of adipose progenitor cells, culturing the population of adipose progenitor cells such that at least one adipocyte progenitor cell is induced to differentiate to a brown adipocyte and preparing the brown adipocyte as an injectable composition for implantation into a target region in the subject where the brown adipocyte is able to thrive.

In one embodiment of the invention, the vector can be a viral vector or a non-viral vector. Non-limiting examples of viral vectors can be adenoviral vector, adeno-associated viral vector, lentiviral vector, lentiviral vector and herpes virus vector. The vectors can be introduced in vivo or in vitro.

The vector can be capable of expressing a gene. The vector can further introduce a gene whose protein product is capable of modulating uncoupling protein activity. The protein product can be uncoupling protein 1 (UCP1), uncoupling protein 2 (UCP2), uncoupling protein 3 (UCP3), uncoupling protein 4 (UCP4), and uncoupling protein 5 (UCP5). The vector can include a gene for a receptor. The receptor can increase uncoupling protein activity. The receptor can be thyroid hormone receptor (TR), peroxisome proliferators-activated receptor (PPAR), β-adrenergic receptor, transforming growth factor receptor, free fatty acid receptor and low density lipoprotein receptor. Alternatively, the receptor can be a hybrid receptor with at least a portion of the receptor derived from thyroid hormone receptor (TR), peroxisome proliferators-activated receptor (PPAR), β-adrenergic receptor, transforming growth factor receptor, free fatty acid receptor and low density lipoprotein receptor. The hybrid receptor can further include at least a portion of a receptor selected from a β-adrenergic receptor and a transforming growth factor receptor.

The vector can also be operatively linked to an inducible promoter. The promoter can be inducible in the presence of at least one of light, hormones, growth factors, cytokines, heavy metals, receptor ligands, receptor agonists and receptor antagonists. Additionally, the promoter can be inducible in the presence of at least one of fatty acids, glucose, insulin, cAMP, lipoproteins, norepinephrine and acetylcholine. The receptor gene can also be under the control of an inducible promotor.

In another embodiment of the invention, brown adipose tissue can be augmented by providing at least one adipose progenitor cell, culturing the adipose progenitor cell to induce differentiation and transplanting the brown adipocyte into a tissue target region in the subject. Target tissues can include brown tissue targets such as supraclavicular region, a nape of a neck, a scapula, a spinal cord, and around at least one kidney, under the renal capsule, the liver, the skin, or elsewhere. The injectable composition can also be transplanted into a target region, such as a supraclavicular region, a nape of a neck, a scapula, a spinal cord, around at least one kidney, the renal capsule, the liver, and the skin.

Furthermore, the adipose progenitor cell can be a mesenchymal stem cell, a preadipocyte and a adipocyte precursor cell. The adipose progenitor cell can be obtained from or harvested from bone marrow, peripheral blood, umbilical cord blood, skeletal muscle, cardiac muscle, and brown adipose tissue. Moreover, the adipose progenitor cell can be heterologous or autologous to the subject.

A composition For modifying brown adipose tissue earl also include at least one adipocyte and a pharmaceutically acceptable carrier. The adipocyte can be a brown adipocyte, an adipocyte progenitor cell and/or heterologous or autologous to a subject.

In one more embodiment, the adipose progenitor cell and/or the adipocyte can be modified to express a gene capable of increasing uncoupling protein activity. The modified adipose progenitor cell and/or the brown adipocyte can be expanded in culture and then returned to brown adipose target tissues to treat metabolic disorders such as obesity, diabetes and hyperlipidemia.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
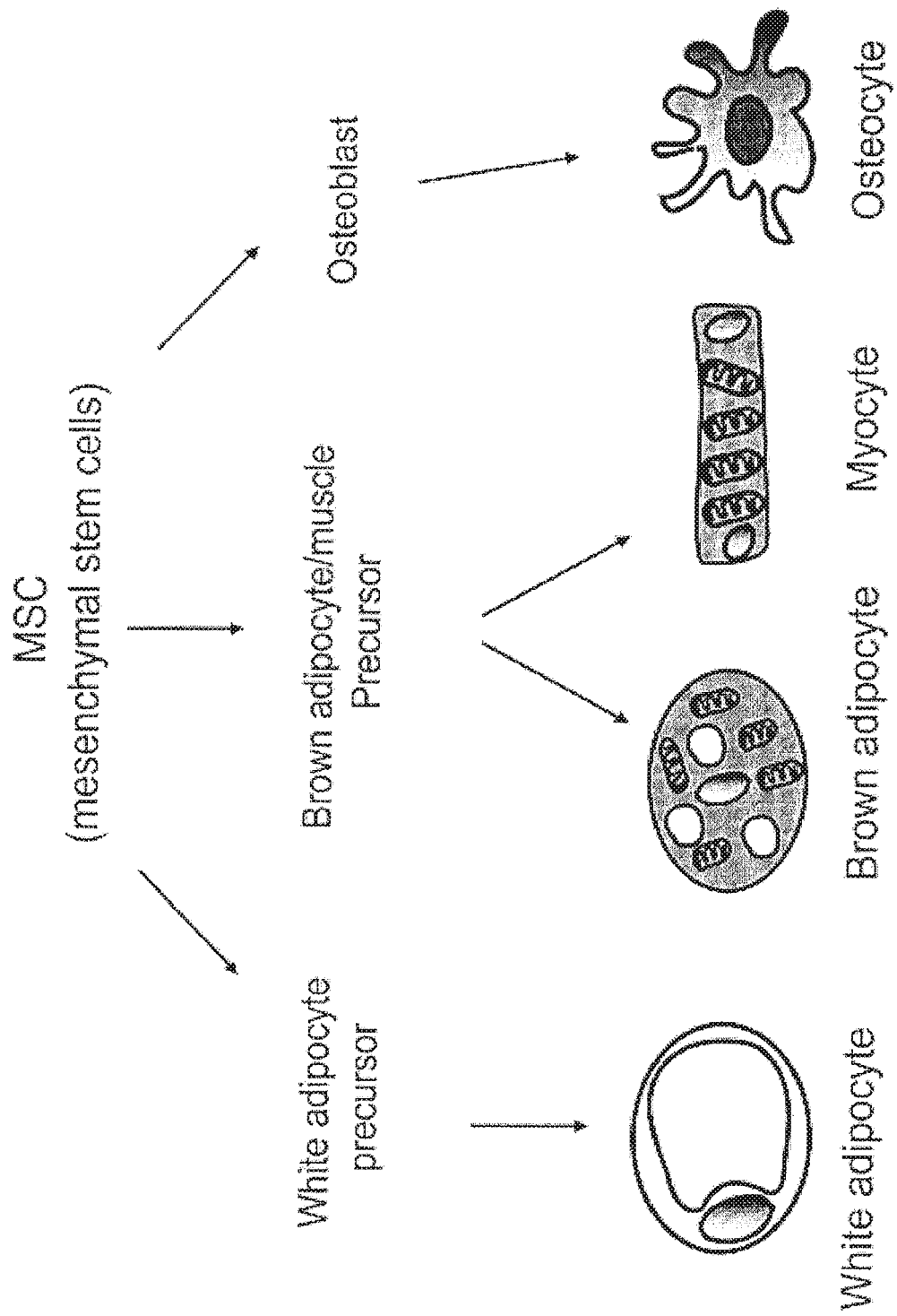
FIG. 1 is an illustration of mesenchymal stem cell differentiation into white adipocytes, brown adipocytes, myocytes and osteocytes.

Certain exemplary embodiments will now be described to provide an overall understanding of the principles of the structure, function, manufacture, and use of the therapeutics and methods disclosed herein. One or more examples of these embodiments are illustrated in the accompanying drawings. Those skilled in the art will understand that the therapeutics and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, the present invention provides methods and compositions for increasing the effectiveness of brown adipose tissue (BAT) and brown adipocytes to treat metabolic disorders, such as obesity, diabetes and hyperlipidemia. The methods and compositions disclosed are useful to increase the amount of and/or the ease of activation of BAT through techniques including modification of brown adipocyte signaling, such as activation of the uncoupling protein (UCP) signaling. Modification of adipocytes can include increasing expression of uncoupling protein to activate UCP activity and/or expressing hybrid receptors capable of selectively activating UCP signaling. The brown adipocytes can be modified and subsequently returned to a BAT reservoir or another site in a subject, thereby increasing the amount of activated BAT.

Further, activation of UCP can be increased through modifications to brown adipocytes and/or expression of hybrid receptors in brown adipocytes. UCP activation can be induced through physical and chemical stimulation or signaling through upstream receptors of UCP or can be constitutively activated to treat the metabolic disorder. Methods and pharmaceutical compositions to activate an upstream receptor or a hybrid receptor including regulatory proteins, ligands, agonists and antagonists can be used. Examples of such include fatty acids, cAMP, receptor ligands, norepinephrine, acetylcholine, and growth factors (TGFRβ1) etc. Another related approach is to use an inducible promoter to drive expression of a gene encoding a signaling protein whose expression leads to activation of UCP-1 and, thereby, BAT.

Furthermore, methods and compositions arc also disclosed to increase BAT activation by increasing the total amount of BAT in a subject. This can be achieved through multiple mechanisms, such as differentiation of stem cells to brown adipocytes, recruitment of stem cells to BAT depots in the body and subsequent differentiation into brown adipocytes and transplantation of stem cells and/or brown adipocytes to BAT depots. Moreover, the above mentioned methods can be combined with brown adipocyte modification to further increase the level of BAT activation, or the activation of "beige" or "brite" cells in white adipose tissue, in a subject.

Brown Adipose Tissue

Adipocytes are central to the control of energy balance and lipid homeostasis. Tile ability to store excess energy in adipose tissue is an important evolutionary adaptation. There are two types of fat or adipose tissue: white adipose tissue (WAT), the primary site of energy storage, and brown adipose tissue (BAT), specialized for energy expenditure and thermogenesis.

Intriguingly, an inverse correlation exists between the amount of brown adipose tissue and body mass index, with obese individuals having significantly less of the tissue than lean individuals; this suggests that brown fat may be an important factor in maintaining a lean phenotype or that the obese phenotype has led to the diminution in size and/or activity of the BAT depots. Obesity typically refers to an individual having a body mass index (BMI) of 30 kg/m$^2$ or more. Overweight describes an individual having a body mass index (BMI) of 25 kg/m$^2$ or greater, but less than 30 kg/m$^2$ or an individual who has a desire to lose weight regardless of their BMI or a non-obese individual that manifests a metabolic disease, such as diabetes or hyperlipidemia. BMI is a measure expressing the relationship (or ratio) of weight-to-height based on a mathematical formula in which a person's body weight in kilograms is divided by the square of his or her height in meters (i.e., wt/(ht)$^2$). See National Institute of Health, Clinical Guidelines on the Identification, Evaluation, and Treatment of Overweight and Obesity in Adults (1998).

Adipose tissue is composed, in part, of adipocytes or fat cells specific for WAT or BAT. Adipocytes can also produce adipokines, such as TNFα, leptin, resistin, RBP4, apelin, and adiponectin, to modulate systemic metabolism. The inability to properly store triglycerides in adipose tissue results in adverse effects on glucose metabolism in the liver and skeletal muscle. In contrast with WAT, the physiological role of BAT is to metabolize fatty acids and generate heat. This specialized function of brown fat cells derives from high mitochondrial content and the ability to uncouple cellular respiration through the action of uncoupling protein-1 (UCP-1). Due to these functional differences, the balance between WAT and BAT affects systemic energy balance and may contribute to the development of obesity.

Most brown fat cells and muscle cells both seem to be derived from the same stem cells in the embryo. Both have the same marker on their surface (myogenic factor 5, Myf5), which white fat cells do not express. Brown fat cells and muscle cells both come from the middle embryo layer, or mesoderm, the source of myocytes (muscle cells), adipocytes, and chondrocytes (cartilage cells). See, FIG. 1. There is a second population of brown adipocytes within WAT—sometimes called "beige" or "brite" adipocytes—that derives from white adipocytes and appears to be from an independent (myf5-negative lineage).

Mesenchymal stem cells give rise to precursor cells of bone, muscle, and fat cells under appropriate conditions. Adipogenesis is generally described as a two-step process. The first step comprises the generation of committed adipocyte precursors preadipocytes) from mesenchymal stem cells (MSCs). The second step involves the terminal differentiation of these preadipocytes into mature functional adipocytes. By definition, MSCs are endowed with self-renewal properties and a differentiation potential towards all mesenchymal cell types, whereas preadipocytes have lost the ability to differentiate into mesenchymal derivatives other than adipocytes. Adipocytes, in turn, can be classified as either white fat cells or brown fat cells.

Signaling Activation in BAT Cells

In one aspect of the invention, methods and compositions are disclosed to increase activation of BAT through modification of brown adipocyte signaling. BAT cells can be modified by expressing key signaling molecules that increase fatty acid metabolism and optimize energy expenditure to treat or prevent obesity.

Exposure to cold leads to sympathetic stimulation of brown adipocytes via norepinephrine binding to beta-adrenergic receptors. Within brown adipocytes, most fatty acids are immediately oxidized in mitochondria and, because of uncoupling proteins, a large amount of heat is produced. This process is part of what is called non-shivering thermogenesis.

Non-shivering thermogenesis requires a signaling cascade leading to an activation of adipocyte fatty acid metabolism. In contrast to other cells, including white adipocytes, brown adipocytes express mitochondrial UCP1 (SEQ ID NO:1nucleic acid sequence and SEQ ID NO:2, protein sequence), UCP2 (SEQ ID NO:3, nucleic acid sequence and SEQ ID NO:4, protein sequence), UCP3 (SEQ ID NO:5, nucleic acid sequence and SEQ ID NO:6, protein sequence), UCP4 (SEQ ID NO:7, nucleic acid sequence and SEQ ID NO:8, protein sequence) and UCP5 (SEQ ID NO:9, nucleic acid sequence and SEQ ID NO:10, protein sequence), which give the cell's mitochondria an ability to uncouple oxidative phosphorylation and utilize substrates to generate heat rather than ATP.

Figure 2:
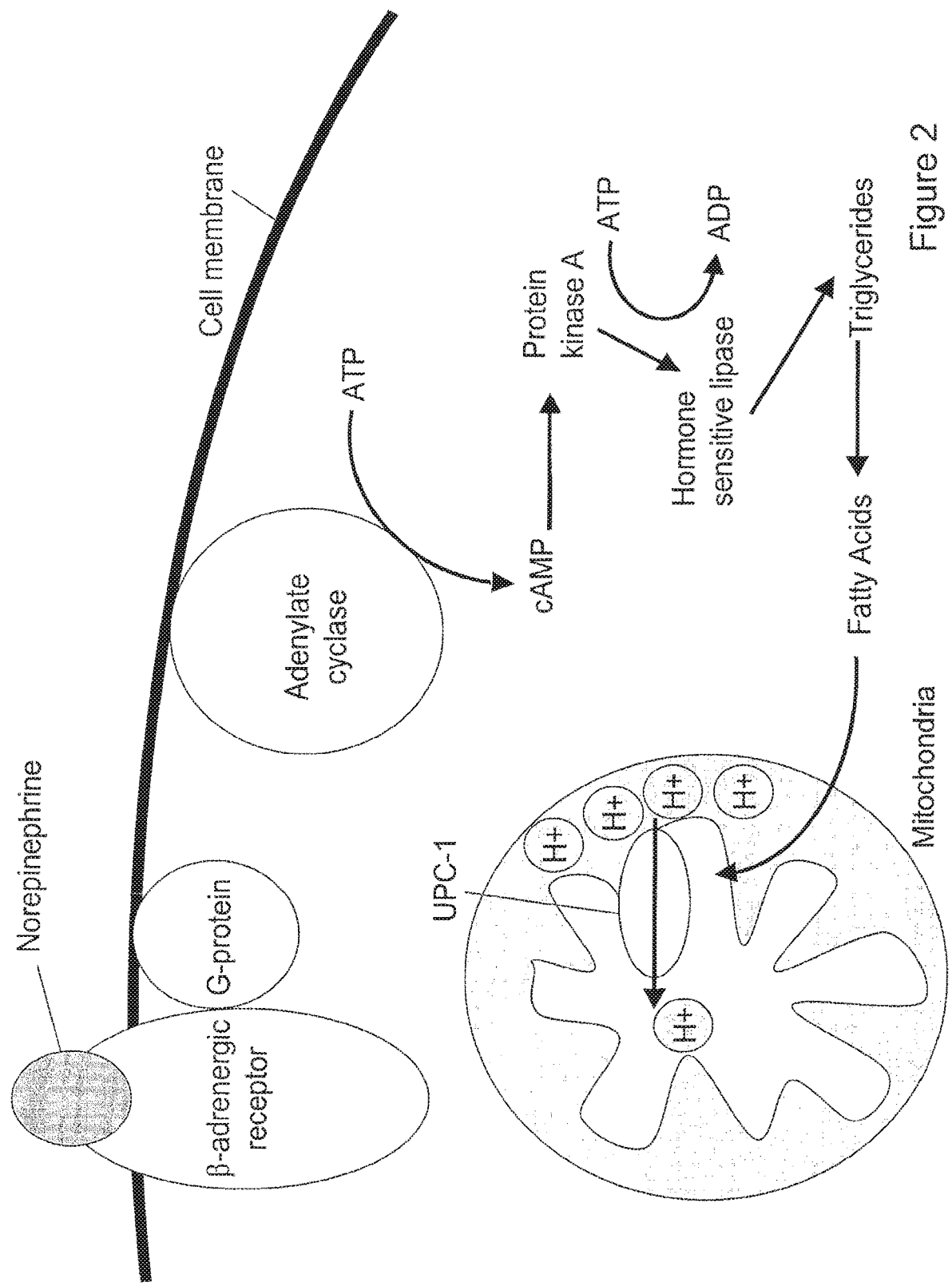
FIG. 2 is a schematic drawing of β-adrenergic signaling resulting in activation of uncoupling protein 1 (UCP1) in the mitochondria.

UCPs are transmembrane proteins that discharge the proton gradient generated in oxidative phosphorylation (FIG. 2). They do this by increasing the permeability of the inner mitochondrial membrane, allowing protons that have been pumped into the intermembrane space to rein mu to the mitochondrial matrix without coupling this process to ATP formation. UCPs are related to other mitochondrial metabolite transporters, such as the adenine nucleotide translocator, a proton channel in the mitochondrial inner membrane that permits the translocation of protons from the mitochondrial intermembrane space to the mitochondrial space. In particular, UCP1 is largely restricted to brown fat, where it provides a mechanism for the enormous heat-generating capacity of the tissue. UCP1-mediated heat generation in brown fat uncouples the respiratory chain, allowing for fast fatty acid oxidation with a low rate of ATP production.

Figure 3:
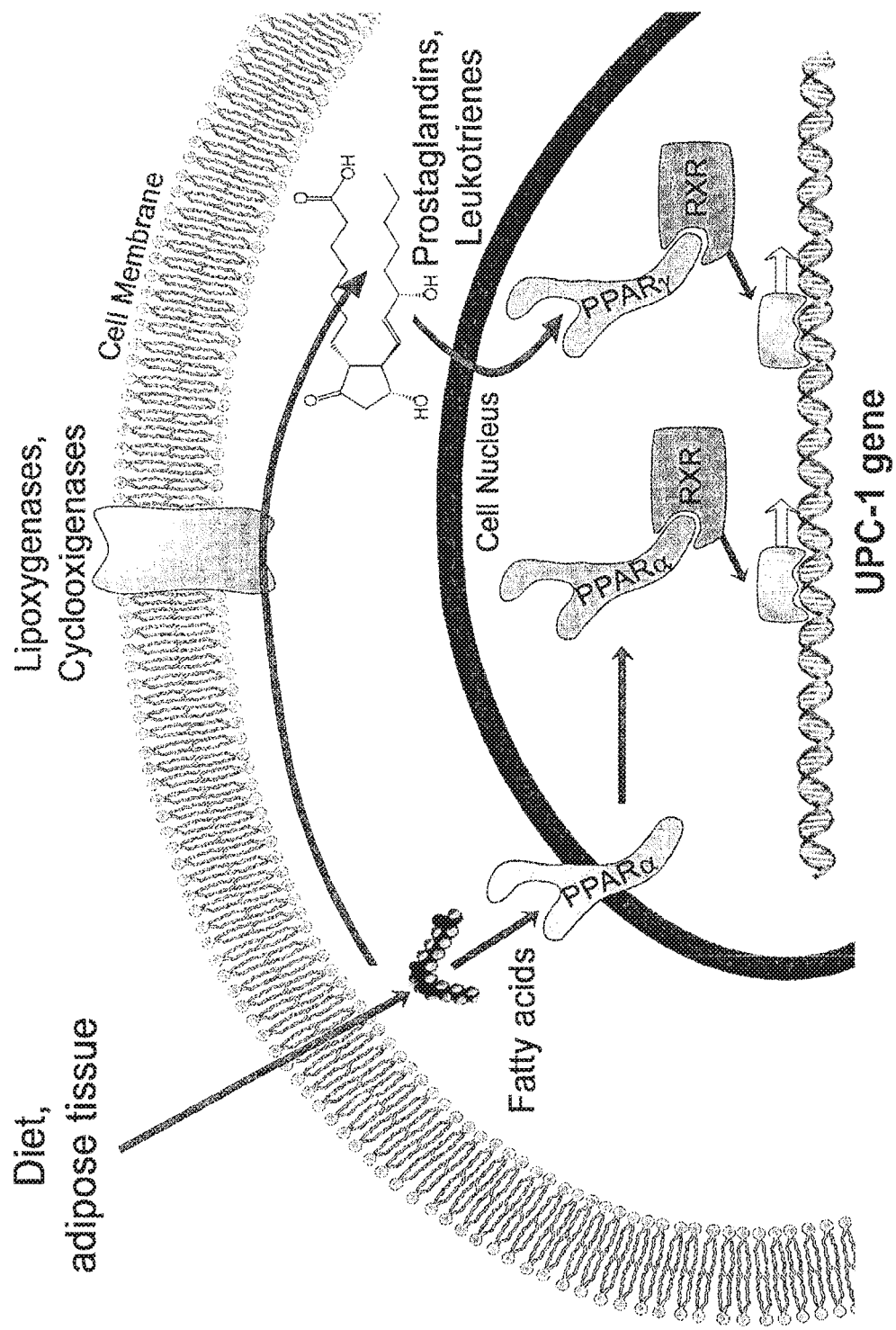
FIG. 3 is a schematic drawing of fatty acid translocation and binding to peroxisome proliferator-activated receptor (PPAR) heterodimers with retinoid activation receptor to activate UCP-1 gene expression.

Thyroid hormone receptor (TR) and peroxisome proliferators-activated receptor (PPAR) are two nuclear hormone receptors which also play essential roles in UCP-1 gene expression and BAT cell activation. PPAR's ability to promote BAT cell differentiation, sterns from the binding of a PPAR/retinoid X receptor (RXR) heterodimer to an enhancer sequence in the UCP-1 gene (FIG. 3). This binding, however, is specific to brown adipocytes.

In one aspect, methods and composition are disclosed to activate an uncoupling protein in adipocytes, such as BAT cells. The UCP can be activated by providing a full-length, portion or fragment of the uncoupling protein gene and expressing the full-length, portion or fragment of the uncoupling protein gene in the adipocytes, such as BAT cells. The term "full-length UCP" refers to the entire open reading frame, capable of expressing a full-length UCP protein. A "portion" or "fragment" of the protein encoded by the UCP gene refers to an amino acid sequence that has fewer amino acids than the entire sequence of the UCP protein. A fragment can comprise any desired domain within UCP. Sizes of peptide fragments can be designed to be less than about 200 amino acids, less than about 100 amino acids, less than about 80 amino acids, less than about 60 amino acids, less than about 40 amino acids, less than about 20 amino acids, and less than about 10 amino acids, so long as the peptide fragment retains a desired activity.

In another aspect, methods and compositions are disclosed to activate an uncoupling protein signaling cascade in adipocytes by providing a gene for a hybrid receptor that is capable of selectively activating uncoupling protein signaling in the adipocytes. Hybrid receptor genes of the invention can include at least a portion of a receptor such as a β-adrenergic receptor (SEQ ID NO: 11) or a transforming growth factor receptor (SEQ ID NO:12), fused to an extracellular domain capable of binding fatty acids, cholesterol and/or glucose. The hybrid receptors can also include at least a portion of a peroxisome proliferator-activated receptor, free fatty acid receptor 1 (SEQ ID NO:13), free fatty acid receptor 2 (SEQ NO:14), and cholesterol receptors such as the low density lipoprotein receptor (SEQ ID NO:15).

Hybrid receptors can be inducible in the presence of ligand or agonist. Many different ligands can be used to effect control over hybrid promoters, including small molecules, regulatory proteins, ligands, agonists and antagonists. In one embodiment, the ligand can be glucose. In another embodiment, the ligand can be a fatty acid. In yet another embodiment, the ligand can be produced by exposure to an energy source. In one more embodiment, the ligand can be produced by exposure to light. In one more embodiment, the ligand can be a cAMP molecule. One skilled in the art will appreciate that it is also possible to express non-hybrid receptors or other signaling molecules to activate UCP.

In one embodiment, the UCP gene, a portion of the UCP gene and/or a hybrid receptor gene can be expressed in adipocytes. The gene can be transcribed and translated into a protein and converted into an operational or structural part of the adipocyte. Expression of the gene can be measured, for example, by levels of RNA (such as, mRNA) in a cell, or protein expression. Methods of determining RNA levels are well known in the art, and include Northern blots, RT-PCR, RNAse protection, and others. Methods of determining protein expression are well known, and can include Western blots, functional assays, immunofluorescence, optical absorbance, microscopy (including electron microscopy) and others.

Altering expression of genes like UCPs or expressing hybrid receptors can provide a mechanism to treat those with metabolic disorders that result in excessive weight gain, such as obesity, diabetes and hyperlipidemia. Gene therapy methods to increase or improve activation of UCP signaling can also be accomplished by methods known to those skilled in the art. For example, delivering a gene capable of expressing UCPs or a hybrid receptor to activate UCP signaling can be delivered to adipocytes, such as BAT cells. In return, the in-vivo steady state level of UCP activation can be increased, through augmented expression of UCPs, drug, delivery to activate UCP signaling cascades, upstream receptor stimulation and increased sensitivity of UCP activation in BAT cells to treat metabolic disorders.

Vector Systems

One aspect of the invention is directed to altering activation of BAT cells through alteration of genes to treat metabolic disorders. This can be accomplished by delivery (such as by a vector) of a gene capable of expressing the UCP gene, a portion of the UCP gene and/or a hybrid receptor gene capable of inducing expression of a UCP gene.

The UCP gene, a portion of the UCP gene and/or a hybrid receptor gene capable of inducing expression of a UCP gene can be administered to the adipocytes, or BAT cells, by means of a vector. Vectors can be used to genetically alter the adipocytes of the present invention and their progeny. Vectors can be used to deliver one or more target genes, such as UCP genes, hybrid receptor gene, polynucleotides, antisense molecules, or ribozyme sequences, for example, into the cells. Vectors and methods for using them to deliver DNA to cells are well known to those of skill in the art. Examples of vectors which can be used to genetically alter the cells of the present invention include, but are not limited to, non-viral vectors and viral vectors.

Additionally, the vector can include a promoter to regulate expression of the gene. A "promoter" refers to a DNA sequence operatively linked to the gene to which RNA polymerase can bind to initiate the transcription of the gene. In general, the gene or coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of different lengths may have identical promoter activity. The term "promoter region" includes promoter and adjacent areas whose function may be modulate promoter activity.

In one embodiment, a tissue specific promoter can be used to enable operation of the vector in adipose cells. Examples of promoters for adipocytes include but are not limited to, preadipocyte promoters (e.g., 422(aP2) promoter; Cheneval et al. (1991) *Proc. Natl. Acad. Sci. USA* 88:8465-9) and CYP19A1 promoter (Zhao et al. (2009) *Reproduct. Biol Endrocrin.* 7: 37-45). Preferably, the promoter is tissue specific and is essentially not active outside adipose tissue, or the activity of the promoter is higher in adipose tissue than in other tissues. The promoter may also be one that can be used in combination with a viral terminal repeat to result in higher expression. Promoters which cause a gene to be expressed in most cell types at most times are commonly referred to as "constitutive promoters." For example, a cytomegalovirus enhancer/chicken-Actin (CBA) hybrid promoter that functions in cells of the CNS (Xu et al. (2001) *Hum Gene Ther.* 12:563-73).

In another embodiment, a promoter can be inducible through response to a regulator, such as cellular conditions, inducer molecules or stimuli. Regulatable promoters include inducible promoters, which are usually "off," but which may be induced to turn "on," and "repressible" promoters, which are usually "on," but may be turned off. Many different regulators are known to effect control over the activity of regulatable promoters, including temperature, hormones, growth factors, cytokines, heavy metals, and regulatory proteins. In one embodiment, the promoter can be inducible through exposure to glucose. In another embodiment, the promoter can be inducible through exposure to fatty acids. In yet another embodiment, the promoter can be inducible through exposure to an energy source. In one more embodiment, the promoter can be inducible through exposure to light. In one more embodiment, the promoter can be inducible through exposure to cAMP, norepinephrine or acetylcholine. In another embodiment, the promoter can be inducible through exposure to insulin. In yet another embodiment, the promoter can be inducible through exposure to cholesterol, such as lipoproteins.

In another embodiment, viral vectors can used to express the gene. Viral vectors can include adenoviral vectors, adeno-associated viral vectors, retroviral vectors (including lentiviral vectors), lentiviral vectors (e.g., Sindbis vectors), and herpes virus vectors.

Retroviral vectors are effective for transducing rapidly-dividing cells, although a number of retroviral vectors have been developed to effectively transfer DNA into non-dividing cells as well (Mochizuki, H., et al., J. Virol. (1998) 72: 8873-8883). Packaging cell lines for retroviral vectors are known to those of skill in the art. Packaging cell lines provide the viral proteins needed for capsid production and virion maturation of the viral vector. Generally, these include the gag, pol, and env retroviral genes. An appropriate packaging cell line is chosen from among the known cell lines to produce a retroviral vector which is ecotropic, xenotropic, or amphotropic, providing a degree of specificity for retroviral vector systems A retroviral DNA vector is generally used with the packaging cell line to produce the desired target sequence/vector combination within the cells. Briefly, a retroviral DNA vector is a plasmid DNA which contains two retroviral long terminal repeats (LTRs) positioned about a multicloning site and SV40 promoter so that a first LTR is located 5 to the SV40 promoter, which is operationally linked to the target gene sequence cloned into the multicloning site, followed by a 3 second LTR. Once formed, the retroviral DNA vector can be transferred into the packaging cell line using calcium phosphate-mediated transfection, as previously described. Following approximately 48 hours of virus production, the viral vector, now containing the target gene sequence, is harvested.

Targeting of retroviral vectors to specific cell types can also be used with the methods and composition of the present invention. Where targeted delivery is desired, as, for example, when differentiated cells are the desired objects for genetic alteration, retroviral vectors fused to antibody fragments directed to specific markers expressed by adipocytes can be used to target delivery to those cells.

Lentiviral vectors can also be used to genetically alter cells of the invention. Many such vectors have been described in the literature, and are known to those of skill in the art. Salmons, B. and Gunzburg, W. H., "Targeting of Retroviral Vectors for Gene Therapy," Hum. Gene Therapy (1993) 4: 129-141. These vectors have been effective for genetically altering human hematopoietic stem cells (Sutton, R., et al., J. Virol. (1998) 72: 5781-5788). Packaging cell lines have been described for lentivirus vectors (see Kafri, T. et al., J. Virol. (1999) 73: 576-584; Dull, T., et al., J. Virol. (1998) 72: 8463-8471).

Recombinant herpes viruses, such as herpes simplex virus type I (HSV-1), can also be used to genetically alter the cells of the present invention.

Adenoviral vectors can be especially useful having a high transduction efficiency and the ability to incorporate DNA inserts up to 8 Kb in both replicating and differentiated cells. A number of adenoviral vectors have been described in the literature and are known to those of skill in the art (see, for example, Davidson, B. L., et al., Nature Genetics (1993) 3: 219-223; Wagner, E., et al., Proc. Natl. Acad. Sci. USA (1992)89: 6099-6103). Methods for inserting target DNA into an adenovirus vector are known to those skilled in the art of gene therapy, as are methods for using recombinant adenoviral vectors to introduce target DNA into specific cell types (see Wold, W., Adenovirus Methods and Protocols, Humana Methods in Molecular Medicine (1998), Blackwell Science, Ltd.). A system has also been described for propagating adenoviral vectors with genetically modified receptor specificities to provide transductional targeting to specific cell types (Douglas, J., et al., Nature Biotech. (1999) 17: 470-475).

Alphavirus vectors, particularly the Sindbis virus vectors, are also available for transducing the cells of the present invention. These vectors are commercially available (Invitrogen, Carlsbad, Calif.) and have been described in, for example, U.S. Pat. No. 5,843,723, as well as by Xiong, C., et al., Science (1989) 243: 1188-1191; Bredenbeek, P. J., et al., J. Virol. (1993) 67: 6439-6446; and Frolov, I., et al., Proc. Natl. Acad. Sci. USA (1996) 93: 11371-11377.

Adeno-associated viral (AAV) vectors can also be constructed using known techniques. The nucleotide sequences of AAV inverted terminal repeat (ITR) regions are known. The skilled artisan will appreciate that AAV ITR's can be modified using standard molecular biology techniques. Additionally, AAV ITRs may be derived from any of several AAV serotypes, including but not limited to, AAV-1 AAV-2, AAV-3, AAV-4, AAV-5, AAVX7, and the like. Furthermore, 5' and 3' ITRs which flank a selected nucleotide sequence in an AAV expression vector need not necessarily be identical or derived from the same AAV serotype or isolate, so long as the ITR's function as intended, i.e., to allow for excision and replication of the bounded nucleotide sequence of interest when AAV rep gene products are present in the cell.

The skilled artisan can appreciate that regulatory sequences can often be provided from commonly used promoters derived from viruses such as, polyoma, Adenovirus 2, cytomegalovirus and Simian Virus 40 for use in the vectors described. Use of viral regulatory elements to direct expression of the protein can allow for high level constitutive expression of the protein in a variety of host cells. Ubiquitously expressing promoters can also be used including, for example, the early cytomegalovirus promoter Boshart et at. (1985) Cell 41:521-530, herpesvirus thymidine kinase (HSV-TK) promoter (McKnight et at. (1984) Cell 37: 253-262), β-actin promoters (e.g., the human β-actin promoter as described by Ng et al. (1985) Mol. Cell Biol. 5: 2720-2732) and colony stimulating factor-1 (CSF-1) promoter (Ladner et al. (1987) EMBO J. 6: 2693-2698).

In order to produce recombinant viral particles, a viral vector can be introduced into a suitable host cell using known techniques, such as by transfection. A number of transfection techniques are generally known in the art. See, e.g., Graham el al. (1973) Virology, 52:456, Sambrook et al. (1989) Molecular Cloning, a laboratory manual, Cold Spring Harbor Laboratories, N.Y., Davis et al. (1986) Basic Methods in Molecular Biology, Elsevier, and Chu et al., (1981) Gene 13:197, Particularly suitable transfection methods include calcium phosphate co-precipitation (Graham et al, (1973) Virol. 52:456-467), direct micro-injection into cultured cells (Capecchi (1980) Cell 22:479-488), electroporation (Shigekawa et al. (1988) BioTechniques 6:742-751), liposome mediated gene transfer (Mannino et al. (1988) BioTechniques 6:682-690), lipid-mediated transduction (Feigner et al, (1987) Proc. Natl. Acad. Sci. USA 84:7413-7417), and nucleic acid delivery using high-velocity microprojectiles (Klein et al. (1987) Nature 327:70-73).

Suitable host cells for producing recombinant viral particles include, but are not limited to, microorganisms, yeast cells, insect cells, and mammalian cells, that can be, or have been, used as recipients of a exogenous nucleic acid molecule. Thus, the term a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed. Non-limiting examples include CHO dhfr-cells, 293 cells or myeloma cells like SP2 or NS0. In one embodiment, cells from the stable human cell line, 293 (readily available through, e.g., the ATCC under Accession No. ATCC CRLI1573) are preferred in the practice of the present invention. Particularly, the human cell line 293, which is a transformed human embryonic kidney cell line. The 293 cell line is readily transfected, and provides a particularly convenient platform in which to produce recombinant virions Protocols for producing recombinant retroviruses and for infecting cells in vitro or in vivo with such viruses can be found in Current Protocols in Molecular Biology, Ausubel et al, (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include Crip, Cre, 2 and Am. See e.g., Berkner al. (1988) BioTechniques 6:616; Rosenfeld et al. (1991) Science 252:431-434; and Rosenfeld et al. (1992) Cell 68:143-155.

In one embodiment, at least a portion of the UCP gene, a portion of the UCP gene and/or a hybrid receptor gene capable of inducing expression of a UCP gene can be incorporated into a vector, such as a viral vector. The vector can be constructed using known techniques to provide at least the UCP gene operatively linked to control elements including a transcriptional initiation region, a exogenous nucleic acid Molecule, a transcriptional termination region and at least one post-transcriptional regulatory sequence. The control elements can be selected to be functional in the adipocyte. The resulting construct which contains the UCP gene, a portion of the UCP gene and/or a hybrid receptor gene capable of inducing expression of a UCP gene can be operatively linked to control components and flanked at the 5' and 3' region with functional ITR sequences. The vector can then be administered by gene transfer therapy or viral vector delivery to the adipocyte (in vivo or ex vivo) or BAT depot in the subject.

In one embodiment, adipocytes, such as BAT cells, can be transduced by a virus containing the UCP gene, a portion of the UCP gene and/or a hybrid receptor gene capable of inducing expression of a UCP gene. Transduced cells can become "transformed" by the nucleic acid when the DNA becomes stably replicated by the cell, either by incorporation of the nucleic acid into the cellular genome, or by episomal replication. As used herein, the terms "transformed" and "transformation" encompass all techniques by which a nucleic acid molecule might be introduced into such a cell.

Alternatively, a non-viral vector system can be used. Such a technique includes delivery of the vector to the desired adipocytes in colloidal dispersion systems that include, for example, macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. In order for a liposome to be an efficient gene transfer vehicle, the following characteristics should be present: (1) encapsulation of the genetic material at high efficiency while not compromising the biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al. (1988) *Biotechniques*, 6:682). Examples of suitable lipids liposomes production include phosphatidyl compounds, such as phosphatidylglycerol, phosphatidylcholine, phosphatidylserine, phosphatidylethanolamine, sphingolipids, cerebrosides, and gangliosides. Additional examples of lipids include, but are not limited to, polylysine, protamine, sulfate and 3b -[N-(N'N' dimethylaminoethane) carbamoyl] cholesterol.

Alternatively, the vector can be coupled with a carrier. Exemplary and preferred carriers are keyhole limpet hemocyanin (KLH) and human serum albumin. Other carriers may include a variety of lymphokines and adjuvants such as INF, IL-2, IL-4, IL-8 and others. Means for conjugating a vector to a carrier protein are well known in the art and include glutaraldehyde, m-maleimidobenzoyl-N-hydroxysuccinimide ester, carbodiimyde and bis-biazotized benzidine. The vector can be conjugated to a carrier by genetic engineering techniques that are well known in the art. (See e.g., U.S. Pat. Nos. 4,608,251; 4,601,903; 4,599,231; 4,599, 230; 4,596,792; and 4,578,770).

In another embodiment, the UCP gene, a portion of the UCP gene and/or a hybrid receptor gene capable of inducing expression of a UCP gene can be incorporated into a non-viral vector. The vector can be introduced into the adipocyte by transformation with plasmid vectors or introduction of naked DNA by electroporation, lipofection, and particle gun acceleration.

Formulations to Modify Brown Adipocytes

In one embodiment, compounds are disclosed that are capable of activating UCP signaling cascades in modified BAT cells. Such compounds of the present invention can include, but are not limited to, norepinephrine; acetylcholine; free fatty acid receptor 1; free fatty acid receptor 2; low density lipoprotein receptor; fatty acids; cholesterol; glucose; insulin; other molecules (e.g., growth factors, cytokins, hormones and receptor ligands), and small molecules. Exemplary receptor ligands can include agonists and antagonists to β-adrenergic receptors, transforming growth factor receptors, and peroxisome proliferator-activated receptors.

In another embodiment, vectors and compounds of the present invention can be incorporated into pharmaceutical compositions suitable for administration to a subject to modify and activate BAT cells. A pharmaceutical composition may also comprise a pharmaceutically acceptable vector carrier. As used herein, "pharmaceutically acceptable vector carrier" includes any and all solvents, dispersion media, coatings, antibacterial and antifungal agents, isotonic and absorption delaying agents, and the like that are physiologically compatible. Examples of pharmaceutically acceptable vector carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition.

The compositions of this invention may be administered in a variety of forms. These include, for example, liquid, semi-solid and solid dosage forms, such as liquid solutions injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In one embodiment, the vector is administered by intravenous infusion or injection. In another embodiment, the vector is administered by intramuscular or subcutaneous injection. In another embodiment, the vector is administered perorally. In yet another embodiment, the vector is delivered to a specific location using stereotactic delivery.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the vector in the required amount in an appropriate solvent with one or a combination of ingredients enumerated above, as required, followed by filtered sterilization.

The composition of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art See, e.g., *Sustained and Controlled Release Drug Delivery Systems*, J. R. Robinson, ed., Marcel Dekker, Inc., New York, 1978. The pharmaceutical compositions of the invention may include a "therapeutically effective amount" or a "prophylactically effective amount" of the vectors of the invention. A "therapeutically effective amount" refers to an amount effective, at dosages and for periods of time necessary, to achieve the desired therapeutic result.

A therapeutically effective amount of a composition to modify BAT may vary according to factors such as the disease state, age, sex, and weight of the individual, and the ability of the vector to elicit a desired response in the individual. A therapeutically effective amount is also one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound air the treatment of sensitivity in individuals.

Generation of Brown Adipocytes

Alternatively, or in addition to modification of adipocytes, augmenting the number of BAT cells to increase their activation levels can also provide a mechanism to treat metabolic disorders, such as obesity, diabetes and hyperlipidemia. In one embodiment, brown adipose tissue can he augmented by growth or expansion of adipocytes. The adipocytes can be grown in vivo, through recruitment of brown adipocytes and/or adipocyte progenitor cells to BAT depots in the body and differentiation of adipocyte progenitor cells. Alternatively, adipocytes can be grown ex vivo, by harvesting brown adipocytes and/or adipocyte progenitor cells and differentiating/expanding the cells in culture prior to transplantation into BAT depots or elsewhere in the body.

Adipocytes, such as brown adipocytes, can be expanded by a process that increases the number or amount of cells due to cell division. The terms "adipocyte," "brown adipocyte," and "brown adipose cell," are used interchangeably. The terms "adipocyte." and "adipocyte progenitor cell" as used herein also refer to a cell that can be induced to proliferate. The adipocyte progenitor cell can include, but is not limited to, a pre-adipocyte, an adipocyte precursor cell, skeletal satellite cell, skeletal progenitor cell and cells that can he de-differentiated to produce adipocytes. A progenitor cell is less differentiated than a terminally differentiated, mature adipocyte. The terms "proliferate," "proliferation" or "proliferated" may also be used interchangeably with the words "expand," "expansion," or "expanded."

In one aspect of the invention, brown adipose tissue can be increased or augmented by recruitment of brown adipocytes or progenitor cells that are capable of differentiating into brown adipocytes to BAT depots. Brown adipocytes can be recruited through stimulation. Such stimulation can include, but is not limited to, physical and/or chemical stimulation. Some non-limiting examples can include growth factor, hormone, electric sympathetic stimulation, adrenergic activation and interaction of agonists with receptors such as thyroid hormone receptor (TR) and peroxisome proliferators-activated receptor (PPAR) to recruit brown adipocytes or progenitor cells to BAT depots.

In an alternative embodiment, adipocytes can be removed from the body and cultured on a "feeder-layer" or other type of solid support on which to grow and expand. Any suitable feeder layer can be used with the cells of the present invention. Typically, a suitable feeder layer will support the growth and proliferation of overlaying cells through cell-cell interaction and secretion of soluble growth factors and metabolites into the media. A solid support can also be provided by cultured extracellular matrix proteins such as collagen gel matrix.

Adipocytes can be cultured in any medium or any buffer that maintains the viability and proliferative state of the cells, such as a growth medium. Numerous culture media are known and are suitable for use. Generally, a growth medium includes a minimal essential medium. In one embodiment, the medium is DMEM-low glucose (DMEM-LG). The growth medium may be supplemented with serum. Specific, non-limiting examples of serum are horse, calf or fetal bovine serum (PBS). The medium can have between about 2% by volume to about 10% by volume serum, or about 5% by volume serum, or about 2%. In one embodiment, a growth medium is supplemented with about 5% PBS. In one embodiment, the medium contains one or more additional additives, such as antibiotics or nutrients. Specific non-limiting examples of antibiotics include 10-1000 U/ml penicillin and about 0.01 mg/ml to about 10 mg/ml streptomycin. In a particular example, a growth medium contains about 100 U/ml penicillin and about 1 mg/ml streptomycin.

In another embodiment, additional adipocytes can be generated through differentiation of stem cells. Mesenchymal stem cells (MSC), originally derived from the embryonal mesoderm and isolated from adult bone marrow, can differentiate to form multiple lineages, including fat. A number of mesenchymal stem cells have been isolated from multiple tissues (see, for example, Caplan, A., et al., U.S. Pat. No. 5,486,359; Young, H., et al., U.S. Pat. No. 5,827,735; Caplan, A., at al., U.S. Pat. No. 5,811,094; Bruder, S., et al., U.S. Pat. No. 5,736,396; Caplan, A., et. al., U.S. Pat. No. 5,837,539; Masinovsky, B., U.S. Pat. No. 5,837,670; Pittenger, M., U.S. Pat. No. 5,827,740; Jaiswal, N., et al., J. Cell Biochem. (1997) 64(2): 295-312; Cassiede P., at al., J. Bone Miner, Res, (1996) 11(9): 1264-4273; Johnstone, B., et al., (1998) 238(1): 265-272; Yoo, et al., J. Bone Joint Surg. Am. (1998) 80(12): 1745-1757; Granthos, S., Blood (1994) 84(12): 4164-4173; Makino, S., et al., J. Clin. Invest. (1999) 103(5): 697-705).

As used herein, the term "mesenchymal stem cell" refers to a master cell that can reproduce indefinitely to form the specialized cells of the disclosure. The cell has the potential to differentiate upon appropriate stimulations such as by appropriate growth factors.

Mesenchymal stem cells (MSCs) can also be characterized by surface immunophenotype, transcriptome, cytokine profile, and proteome. Some biomarkers can be used for identification of the MSCs. The terms "biomarker," "surface marker," and "marker" are used interchangeably and refer to a protein, glycoprotein, or other molecule expressed on the surface of a cell, which serves to help identify the cell. Some biomarkers for identification can include, but are not limited to, positivity for CD9, CD29 ($\beta$1-integrin), CD44 (H-CAM), CD73 (5' ectonucleotidase, SH3, SH4), CD81, CD90 (Thy1), CD105 (endoglin), CD122, CD164, and CD166 (ALCAM), and negativity for CD11b/14, CD19/79$\alpha$, CD34, CD45 and CD133. MSCs can further he defined by functional characteristics, such as adherence to plastic surfaces, differentiation capabilities (adipogenic, chondrogenic and osteogenic lineages), production of growth factors (interleukin 6 (IL-6), interleukin 7 (IL-7), macrophage colony stimulating factor and stromal derived factor 1) and release of paracrine cytokines. The cell surface markers can generally be detected by conventional Methods known by those skilled in the art. Specific, non-limiting examples of methods for detection of a cell surface marker are immunohistochemistry, fluorescence activated cell sorting (FACS), or an enzymatic analysis.

MSCs or adipocyte progenitor cells can be isolated from multiple tissues, such as bone marrow, peripheral blood, umbilical cord blood and adipose tissue. MSCs or adipocyte progenitor cells can further be isolated from mononuclear cells from bone marrow, peripheral blood, umbilical cord blood, skeletal muscle, and adipose tissue. The term "isolated" as used herein refers to a cell, a group of cells, a population of cells, a tissue or an organ that has been purified from the other components. Cells can be isolated by a variety of methods, including mechanical and/or enzymatic methods. In one embodiment, an isolated population of cells includes greater than about 50%, greater than about 70%, greater than about 75%, greater than about 80%, greater than about 85%, greater than about 90%, greater than about 95%, greater than about 96%, greater than about 97%, greater than about 98%, or greater than about 99% of the cells of interest. In another embodiment, an isolated population of cells is one in which other cells of a different phenotype cannot be detected. In a further embodiment, an isolated population of cells is a population of cells that includes less than about 15%, less than about 10% of cells, less than about 5% of cells, less than about 4% of cells, less than about 3% of cells, less than about 2% of cells or less than about 1% of cells of a different phenotype than the cells of interest. An "isolated" cell may be a population of clonally derived cells, such as cells expanded into a single-cell-derived colony. The term "essentially" is used to describe a population of cells or a method which is at least 90% effective, at least about 95% effective or at least 98% effective. Thus, a method which "essentially" eliminates a given cell population, eliminates at least about 90% of the targeted cell population, or at least about 98% of the cell population.

In some methods, a subpopulation of cells, which includes MSCs or adipocyte progenitor cells, adheres to a solid substrate (referred to as "adherent cells"), such as a cell culture container (for example, a culture dish, a culture flask, or beads designed for tissue culture). In some embodiments the solid substrate comprises an extracellular matrix (ECM) substrate, ECM substrates include, for example, fibronectin, collagen, laminin, vitronectin, polylysine, tenascin, elastin, proteoglycans (such as, heparan sulfate proteoglycans), entactin, Matrigel™, synthetic RGDS-containing peptides covalently crosslinked to hydrophobic biocompatible scaffolds (such as polyethylene glycol (PEG), poly glycolic acid (PGA), poly(D,L-lactide-co-glycolide) (PLGA), or others), or a combination thereof. Any or all forms of a particular ECM substrate are contemplated herein. For example, collagen is commonly known to occur in multiple isoforms (Molecular Biology of the Cell, 3rd Edition, ed. by Alberts et al., New York: Garland Publishing, 1994, Ch. 19), including eighteen different collagen isoforms (such as collagen I, II, III, IV, V, and others). Similarly, multiple isoforms of laminin (Ekblom et al., Ann. N.Y. Acad. Sci., 857:194-211, 1998) and fibronectin ((Molecular Biology of the Cell, 3rd Edition, ed. by Alberts et al., New York: Garland Publishing, 1994, Ch 19) are known. In specific, non-limiting embodiments, an ECM substrate comprises a 1-1000 ng/ml fibronectin-coated solid substrate, for example a 10 ng/ml fibronectin-coated solid substrate.

In other methods, adherent cells are co-cultured with cells from the biological sample, which do not adhere to a solid substrate and remain in suspension (referred to as "non-adherent cells"). Adherent and non-adherent cells may be co-cultured for various durations, such as for no less than about 3 days, no less than about 5 days, no less than about 7 days, or no less than about 14 days. In a particular example, adherent and non-adherent cells are co-cultured for about 14 days. After which time, non-adherent cells may be removed from the culture. Cells of interest could also be co-cultured with cells that have been prevented from dividing by previous irradiation or by other methods, The culture medium can be any medium or any buffer that maintains the viability of the cells, such as a growth medium. Numerous culture media are known and are suitable for use. Generally, a growth medium includes a minimal essential medium. In one embodiment, the medium is DMEM-low glucose (DMEM-LG). The growth medium may be supplemented with serum. Specific, non-limiting examples of serum are horse, calf or fetal bovine serum (FBS.). The medium can have between about 2% by volume to about 10% by volume serum, or about 5% by volume serum, or about 2%, In one embodiment, a growth medium is supplemented with about 5% PBS. In one embodiment, the medium contains one or more additional additives, such as antibiotics or nutrients. Specific non-limiting examples of antibiotics include 10-1000 mg/ml penicillin and about 0.01 mg/ml to about 10 mg/ml streptomycin. In a particular example, a growth medium contains about 100 U/ml penicillin and about 1 mg/ml streptomycin.

In one embodiment, the cells are cultured in the growth medium for about 7 days to about 20 days. In another embodiment, the cells are cultured in the growth medium for about 12 days to about 16 days. In a particular embodiment, the cells are cultured in the growth medium for about 14 days. Thereafter, single-cell-derived colonies of mesenchymal stem cells may be isolated for expansion using any technique known in the art, such as cloning rings. Alternatively, single-cell-derived colonies of mesenchymal stem cells may be pooled for expansion.

Separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (for example, positivity for CD9, CD29 ($\beta$1-integrin), CD44 (H-CAM), CD73 (5' ectonucleotidase, SH3, SH4), CD81, CD90 (Thy1), CD105 (endoglin), CD: 22, CD164, and CD166 (ALCAM), and negativity for CD11b/14, CD19/79$\alpha$, CD34, CD45 and CD133) to bind to the solid-phase linked antibodies. The bound cells are then separated from the solid phase by any appropriate method, depending mainly upon the nature of the solid phase and the antibody employed. Antibodies may be conjugated to biotin, which then can be removed with avidin or streptavidin bound to a support or fluorochromes, which can be used with a fluorescence activated cell sorter (FACS), to enable cell separation.

Other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

MSCs, adipocyte progenitor cells, pre-adipocytes and adipocyte precursor cells can be induced to differentiation into adipocytes useful with the present disclosure. The term "differentiation" as used herein refers to a process whereby relatively unspecialized cells (for example, undifferentiated cells, such as multilineage-inducible cells) acquire specialized structural and/or functional features characteristic of mature cells. Similarly, "differentiate" refers to this process. Typically, during differentiation, cellular structure alters and tissue-specific proteins appear. "Adipogenic differentiation" is a process whereby undifferentiated cells acquire one or more properties (for example, morphological, biochemical, or functional properties) characteristic of adipocytes, brown adipocytes. One skilled in the art will appreciate that the "brown adipocytes" include both brown adipocytes that derive from the muscle precursor lineage (myf5-positive lineage) and those that derive directly from white adipocytes (myf5-negative lineage).

Induction of differentiation of MSCs and progenitor cells to adipocytes can be performed by methods known by those skilled in the art. For example, known methods can include, but are not limited to, treatment of MSCs with compounds such as ligands for nuclear hormone receptors (dexamethasone and peroxisome proliferator-activated receptor γ (PPAR γ, pioglitazone, rosiglitazone, Avandia™), indomethacin, insulin, thiazolidinedione, and compounds that increase intracellular levels of cAMP (isobutylmethylxanthine). MSCs and progenitor cells can also be induced to differentiate through expression or overexpression of molecules known to induce differentiation. These can include, but are not limited to, PPARγ, myf5, PRDM16, and bone morphogenetic proteins.

In one embodiment, the adipogenic differentiation medium can include at least hydrocortisone, isobutylmethylxanthine, and indomethacine. In one specific example, the adipogenic medium includes between about 0.2 µM to about 1.0 µM hydrocortisone, such as for example between about 0.3 µM to about 0.7 µM, or between about 0.4 µM to about 0.6 µM hydrocortisone. In yet another example, the adipogenic medium includes about 0.5 µM hydrocortisone. In another embodiment, the adipogenic medium includes between about 0.2 mM to about 1.0 mM isobutylmethylxanthine, such as for example between about 0.3 mM to about 0.7 mM, or between about 0.4 mM to about 0.6 mM isobutylmethylxanthine. In a particular embodiment, the adipogenic medium includes about 0.5 mM isobutylmethylxanthine. In another specific example, the adipogenic medium includes between about 30 µM to about 120 µM indomethacine, such as for example between about 40 µM to about 90 µM, or between about 50 µM to about 70 µM indomethacine. In yet another example, the adipogenic medium includes about 60 µM indomethacine.

Moreover, adipogenic differentiation medium can also contain one or more additional additives, such as one or more antibiotics, growth factors, nutrients, or combinations thereof. Generally, an adipogenic medium includes a minimal essential medium. In one embodiment, the medium is A-MEM (GIBCO-BRL). An adipogenic medium may be supplemented with serum, such as horse, calf, or fetal bovine serum or combinations thereof. An adipogenic medium can have between about 5% by volume to about 25% by volume serum, or about 20% by volume serum, or about 10%. In one embodiment, a growth medium is supplemented with 10% FBS and 10% horse serum. It is further possible to utilize a treatment with bone morphogenic proteins, e.g., BMP7), and transfection of transcriptional regulators such as PRDM16 and PPAR-gamma.

In one, non-limiting example, mesenchymal stem cells and progenitor cells can be contacted with an adipogenic differentiation medium comprising α-MEM, 10% PBS, 10% horse serum, 0.5 µM hydrocortisone, 0.5 mM isobutylmethylxanthine, and 60 µM indomethacine. In a more specific example, the α-MEM is further supplemented with 100 U/ml penicillin and 1 mg/ml streptomycin. Adipogenic differentiation may be expected to occur, for example, in a humidified atmosphere (such as, 100% humidity) of 95% air, 5% CO2 at 37° C. Adipogenic differentiation may be detected between about 1.5 weeks to about 6 weeks. In particular examples, adipogenic differentiation may be detected in about 3 weeks.

Differentiation of mesenchymal stem cells and progenitor cells into adipocytes, such as brown adipose cells, can be measured by any method known to one of skill in the art. Specific, non-limiting examples are immunohistochemical analysis to detect expression of adipose-related polypeptides (for example, lipoprotein lipase or peroxisome proliferators-activated receptor γ-2), or assays such as ELBA assay and Western blot analysis. Differentiation of cells can also be measured by assaying the level of mRNA coding for bone-related polypeptides (for example, lipoprotein lipase or peroxisome proliferators-activated receptor γ-2) using techniques such as Northern blot, RNase protection and RT-PCR. In another embodiment, assays of adipocyte function can be measured, including cytoplasmic accumulation of triglycerides.

Transplantation of Brown Adipose Tissue

In one aspect of the invention, brown adipose tissue can be increased or augmented through transplantation. In one embodiment, BAT can be increased by about 2%-20%. In another embodiment, BAT can be increased by about 5-10%. In another embodiment, BAT can he increased by about 50-100%. In other embodiments, BAT can be increased by at least about 5%, 10%, 20%, 30%, 40%, 50%, 60%, 70%, 80%, 90%, and 100% in either the region of interest or in the patient. The term "transplantation" as used herein refers to the transfer of cells from one body or part of the body to another body or part of the body or from ex vivo to in vivo. An "allogeneic transplantation" or a "heterologous transplantation" is transplantation from one individual to another, wherein the individuals have genes at one or more loci that are not identical in sequence between the two individuals. An allogeneic transplantation can occur between two individuals of the same species, who differ genetically, or between individuals of two different species. An "autologous transplantation" is a transplantation of a tissue or cells from one location to another in the same individual, or transplantation of a tissue or cells from one individual to another, wherein the two individuals are genetically identical.

In one embodiment, cells of the present disclosure, such as modified adipocytes, MSCs, progenitor adipocytes, etc., can be suspended in a suitable transplant media, such as phosphate buffered saline and other salines. The cell transplant mixture can be injected via a syringe with a needle ranging from 30 to 18 gauge, with the gauge of the needle being dependent upon such factors as the overall viscosity of the adipocyte suspension, into a target location. Preferably, needles ranging from 22 to 18 gauge and 30 to 27 gauge can be used.

The term "target site" as used herein refers to a region in the body or a region in a body structure. In some embodiments, the target region can be one or more of the BAT depots discussed herein, e.g., a supraclavicular region, the nape of the neck, over the scapula, alongside the spinal cord, near proximal branches of the sympathetic nervous system that terminate in BAT depots, around at least one of the kidneys, the renal capsule, the liver, the skin, or elsewhere.

One exemplary mode of transplantation is parenteral (e.g., intravenous, subcutaneous, intraperitoneal, intramuscular). In one embodiment, the cells can be injected by intravenous injection. In another embodiment, the cells can be injected by intramuscular or subcutaneous injection. In another embodiment, the cells can be injected perorally. In the most preferred embodiment, the cells can be injected into and delivered to at least one BAT depot.

In addition, target areas where brown adipose tissue has been increased or augmented through transplantation can further undergo BAT activation. Methods of BAT activation can include nerve stimulation and/or direct stimulation of brown adipocytes. Target areas can include any BAT depot selected for activation, such as areas proximate to BAT depots, e.g., a supraclavicular region, the nape of the neck, over the scapula, alongside the spinal cord, near proximal branches of the sympathetic nervous system that terminate in BAT depots, and around at least one of the kidneys.

Identification of one or more BAT depots for activation can be determined on an individualized patient basis by locating BAT depots in a patient by imaging or scanning the patient using PET-CT imaging, tomography, thermography, or any other technique, as will be appreciated by a person skilled in the art. Non-radioactive based imaging techniques can be used to measure changes in blood flow associated with the activation of BAT within a depot.

In one embodiment, a contrast media containing microbubbles can be used to locate BAT. The contrast media can be injected into a patient whose BAT has been activated. An energy source such as low frequency ultrasound can be applied to the region of interest to cause destruction of bubbles from the contrast media. The rate of refill of this space can be quantified. Increased rates of refill can be associated with active BAT depots.

In another embodiment, a contrast media containing a fluorescent media can be used to locate BAT. The contrast media can be injected into a patient whose BAT has been activated. A needle based probe can be placed in the region of interest that is capable of counting the amount of fluorescent contrast that passes the probe. Increased counts per unit time correspond to increased blood flow and can be associated with activated BAT depots. Because humans can have a relatively small amount of BAT and because it can be difficult to predict where BAT is most prevalent even near a typical BAT depot such as the nape of the neck, imaging a patient to more accurately pinpoint BAT depots and can allow more nerves innervating BAT to be stimulated with greater precision. Any number of BAT depots identified through patient imaging can be marked for future reference using a permanent or temporary marker. As will be appreciated by a person skilled in the art, any type of marker can be used to mark a BAT depot, e.g., ink applied on and/or below the epidermis, a dye injection, etc. The marker can be configured to only be visible under special lighting conditions such as an ultraviolet light, e.g., a black light.

Measuring BAT Activation

The present invention also includes methods for assessing BAT activation before, during and/or after modifying the brown adipocytes. Methods of measuring BAT activation can be determined through energy expenditure involving continuous measurements of heat output (direct calorimetry) or inhaled/exhaled gas exchange (indirect calorimetry) in subjects. The term "energy expenditure," as used herein, refers to the amount of energy (calories), that a person uses to breathe, circulate blood, digest food, support routine physiological functions and be physically active. To prevent weight gain, energy intake (caloric intake) must be balanced with energy expenditure.

Measurements of the heat released from a person's body can determine how Much energy an activity has consumed. In addition, indirect calorimetry can measure oxygen consumption, carbon dioxide production and/or nitrogen excretion to calculate a ratio that reflects energy expenditure. A component of energy expenditure can be calculated as basal energy expenditure, which is the amount of energy required to maintain the body's normal metabolic activity, i.e. respiration, body temperature, etc.

Such energy expenditure or metabolic heat production in a subject can be assessed using several techniques. For measurement of the basal metabolic rate, the subject must be within its thermal neutral zone, which is the range of environmental temperatures across which the subject's body temperature can be maintained at its basal metabolic rate. The subject must be in a postabsorptive state, quiescent, in sexual repose, and resting but conscious. Since the latter prerequisite is often difficult to achieve with non-human subjects, the fasting heat production is used for animals which are quiet, but not necessarily resting.

Energy expenditure or metabolic heat production can be detected externally by the subject's heat loss pattern. Radiation, through which 40 to 60% of heat is lost from a subject, can be readily measured using any commercially available pyrometer or temperature sensor, since most radiated heat loss can be displayed in the 5-12 µm wavelength range of the electromagnetic spectrum. Direct and indirect calorimetry are further methods for assessing energy expenditure. Direct calorimetry measures heat loss from a subject directly by placing the subject at rest or exercising in a chamber surrounded by a waterjacket. Heat emitted from the subject raises the temperature of the water. The difference in the temperature of water entering and leaving the chamber reflects the subject's energy expenditure. Indirect calorimetry measures gas exchange and relates it to heat production. Indirect calorimetry involves monitoring of the amount of oxygen consumed (or conversely, the amount of carbon dioxide produced), and calculating the amount of energy expended by the subject, depending on the food substrate being utilized (e.g., fat, carbohydrate or protein).

Metabolic rate can also be measured through the use of doubly labeled water methods in which the average metabolic rate of an organism is measured over time. The use of doubly labeled water methods measures the subject's carbon dioxide production. Oxygen in body water can be lost in carbon dioxide, excretions and evaporative losses. However, hydrogen can only be lost through body water loss. Taking advantage of the change in body water and carbon dioxide production over time can be used to mathematically calculate metabolic rate.

In one embodiment, a dose of doubly labeled water, where the hydrogen and oxygen molecules have been partially or completely replaced with an uncommon isotope, such as deuterium (D or $^2H$) and oxygen-18 (O-18 or $^{18}O$), deuterium oxide-19 ($D_2$ $^{18}O$), or radioactive forms of hydrogen and oxygen, can be administered to the subject and the rate of elimination of the isotope can be measured in the subject over time. Regular sampling of heavy isotope concentrations in body water sources, such as saliva, urine, blood, etc, can be performed. The number of samples and the time between sample collections can be dependent on the size of the subject. Measuring the loss of oxygen isotopes in carbon dioxide production and the loss of oxygen through water-loss can be used to calculate the total metabolic rate.

EXAMPLES

One skilled in the art will appreciate further features and advantages of the invention based on the above-described embodiments. Accordingly, the invention is not to be limited by what has been particularly shown and described in the examples or figures, except as indicated by the appended claims. All publications and references cited herein are expressly incorporated herein by reference in their entirety.
Vector Construction A full length human UCH cDNA can be amplified from 293T cells and cloned into a standard vector. To generate AAV.UCP1, the UCP1 can be PCR-amplified and subcloned into an AAV expression plasmid flanked by inverted terminal repeats. An engineered Kozak consensus translation start site can be included upstream of the UCP1 gene. A control vector can be generated by subcloning the EGFP cDNA into the same AAV backbone or an expression cassette without the transgene can be used as a control (AAV.Empty). Integrity of all constructs can be verified by sequencing.
Viral Production Virus stocks can be prepared by packaging the vector plasmids into AAV particles using a helper-free plasmid transfection system. The vectors can be further purified using heparin affinity chromatography and dialyzed against PBS. Viral titers can be determined by quantitative PCR using AAV enhancer-specific, primers and adjusted to an optimal genomic particles per ml for subsequent use in cell transduction assays. Genomic titers of vector stocks can also be determined using the Perkin-Elmer (PE)-Applied Biosystems (Foster City, Calif.) Prism 7700 sequence detector system as described previously [Clark et al. J. Drug. Target 7, 269-83 (1999)].

The different AAV vectors can be directly injected into brown adipose tissue depots in the mice. The depots include supraclavicular region, the nape of the neck, over the scapula, alongside the spinal cord, near proximal branches of the sympathetic nervous system that terminate in BAT depots, and around the kidneys. Spinal cord injections can be carried out under imaging guidance, such as magnetic resonance imaging, in anaesthetized mice. Control mice can be injected with an equivalent volume of rAAV.empty or rAAV.GFP virus.
BAT Isolation Mice can be used for the preparation of primary cultures of brown adipocytes. At the age of 3-4 wk, mice can be euthanized by $CO_2$, and the BAT can be isolated from the interscapular, cervical, and auxiliary depots, principally as described by Rehnmark et al, in *J Biol Chem* 265:16464-16471, 1990. The pooled tissue pieces can be minced in DMEM and transferred to a digestion solution with 0.2% (wt/vol) collagenase (type II; Sigma) in a buffer consisting of 0.1 M HEPES (pH 7.4), 123 mM NaCl, 5 mM KCl, 1 mM $CaCl_2$, 4.5 mM glucose, and 1.5% (wt/vol) BSA. The digestion can be performed for about 30 min at 37° C. with continuous vortex mixing. The cell suspension can then be filtered through a 250-µm pore-size nylon filter into sterile 15-ml tubes. The filtered suspension can be stored on ice for about 20 min to let the mature adipocytes float up to the top. The top layer of the suspension can be removed, and the rest of the suspension can be filtered through a 25-µm pore-size nylon filter (Sintab) and centrifuged at 700 g for about 10 min, to pellet preadipocytes. The pellet can be resuspended in 10 ml of DMEM and re-centrifuged at 700 g for another 10 min. The pellet can then be suspended in culture medium (0.5 ml/animal).
Cultures The adipocytes and pre-adipocytes can be cultured in six-well plates (10 $cm^2$/well; Corning; 12-well plates for cAMP determination); 1.8 ml of culture medium can be added to each well before cell suspensions are added. The culture medium can be standard adipocyte medium of DMEM with 10% (vol/vol) newborn calf serum (Invitrogen or Hyclone), 2.4 nM insulin, 25 µg/ml sodium ascorbate, 10 mM HEPES, 4 mM glutamine, 50 U/ml penicillin, and 50 µg/ml streptomycin and supplemented or not (as indicated) with 1 µM rosiglitazone maleate (Alexis Biochemicals). The cells can be grown at 37° C. in an atmosphere of 8% $CO_2$, in air with 80% humidity. The cells can be washed in DMEM, and the medium changed on the first day and every second day thereafter.
Differentiation MSCs Differentiation of MSCs to adipocytes. MSC derived from sorted MSCA-1$^+$CD56$^+$ or unfractionated bone marrow cells can be cultured in NH AdipoDiff medium (Miltenyi Biotec, Bergisch Gladbach, Germany), respectively. In brief, $4\times10^4$ (adipogenesis) MSC can be cultured in 24-well Falcon plates (Becton Dickinson, Heidelberg, Germany). The formation of adipocytes can be evaluated after 25 days of culture in NH AdipoDiff medium and stained of methanol-fixed cells can be stained with oil red O dye (Sigma-Aldrich) for 45 min at morn temperature.
Transduction with UCP1 Virus Human adipocytes can be infected with AAV.GFP or AAV.UCP1 at multiplicity of infection (moi) 1,000 for at least 48 h. Conditions can be optimized to yield close to 100% transduction efficiency. Cells can then be treated with MG-132 for 48 h and viability can be determined using Cell Titer 96 Aqueous assay (Promega).
Assessment of Gene Expression RNA can be obtained from the adipocytes and examined by Northern blotting. The membranes can be probed consecutively for aP2, PPARγ, PGC-1α, UCP1 and PPARα mRNAs, and 18S rRNA after being stripped in-between by repeated washing with boiling 0.2% (wt/vol) SDS.
Transplantation Modified adipocytes can be transplanted into brown adipose tissue depots in the mice. The depots include supraclavicular region, the nape of the neck, over the scapula, alongside the spinal cord, near proximal branches of the sympathetic nervous system that terminate in BAT depots, and around the kidneys. Spinal cord injections can be carried out under imaging guidance, such as magnetic resonance imaging, in anaesthetized mice. Control mice can be injected with an equivalent number of rAAV.empty or rAAV.GFP virus transduced cells.
Assessment of BAT Activation through Energy Expenditure Heat released can be measured from the mice transplanted with modified adipocytes to determine energy expenditure and BAT activation. Indirect calorimetry can be measured through oxygen consumption, carbon dioxide production and/or nitrogen excretion to calculate a ratio that reflects energy expenditure before and after transplantation of virally modified brown adipocytes or BAT cell modification.

Terminology

All publications, patents and patent applications cited herein are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. The term does not denote a particular age or sex. In a specific embodiment, the subject is human.

As used herein, the terms "metabolic disorders" and "metabolic diseases" are used interchangeably herein and refer to medical conditions characterized by problems with an organism's metabolism. Since a healthy, functioning metabolism is crucial for life, metabolic disorders are treated very seriously. A broad range of conditions including, but not limited to, diabetes (including type 1 and type 2 diabetes), hyperlipidemia, hypo-thyroidism, and obesity are some examples of disorders that can be classified as metabolic disorders. Metabolic disorders can result in excessive weight gain. The term "metabolic syndrome" refers to a cluster of conditions that occur together, and increase the risk for heart disease, stroke and diabetes. Having just one of these conditions such as increased blood pressure, elevated insulin levels, excess body fat around the waist or abnormal cholesterol levels increases the risk of the above mentioned diseases. In combination, the risk for coronary heart disease, stroke and diabetes is even greater. The main features of metabolic syndrome include insulin resistance, hypertension, cholesterol abnormalities, and an increased risk for clotting. Patients are most often overweight, obese, and/or have a metabolic disorder.

What is claimed is:

1. A composition for modifying brown adipose tissue comprising: at least one adipocyte and a pharmaceutically acceptable carrier,
   wherein the adipocyte is an adipocyte progenitor cell or a brown adipocyte,
   wherein the adipocyte is modified by a vector that expresses a hybrid receptor gene capable of increasing uncoupling protein signaling,
   wherein the hybrid receptor gene comprises a first component comprising at least a portion of a receptor selected from the group consisting of thyroid hormone receptor (TR), peroxisome proliferators-activated receptor (PPAR), β-adrenergic receptor, transforming growth factor receptor, free fatty acid receptor and low density lipoprotein receptor, and combinations thereof, and;

a second component that is different than the first component wherein the second portion comprises at least a portion of a receptor selected from the group consisting of thyroid hormone receptor (TR), peroxisome proliferators-activated receptor (PPAR) β-adrenergic receptor, transforming growth factor receptor, free fatty acid receptor and low density lipoprotein receptor, and combinations thereof.

2. The composition of claim 1, wherein the adipocyte is homologous to a subject.

3. The composition of claim 1, wherein the hybrid receptor further comprises an intracellular domain from a receptor selected from a β-adrenergic receptor and a transforming growth factor receptor.

4. The composition of claim 1, wherein the hybrid receptor gene is under the control of an inducible promoter, wherein the inducible promoter is inducible in the presence of at least one of light, hormones, growth factors, cytokines, heavy metals, receptor ligands, receptor agonists and receptor antagonists.

5. The composition of claim 4, wherein the inducible promoter is inducible in the presence of at least one of fatty acids, glucose, insulin, cAMP, lipoproteins, norepinephrine and acetylcholine.

6. The composition of claim 1, wherein the adipocyte is heterologous to a subject.

7. The composition of claim 1, further comprising a third component that is different than the first component and second component, wherein the third component comprises at least a portion of a receptor selected from the group consisting of thyroid hormone receptor (TR), peroxisome proliferators-activated receptor (PPAR), β-adrenergic receptor, transforming growth factor receptor, free fatty acid receptor and low density lipoprotein receptor, and combinations thereof.

* * * * *